US012655176B2

(12) United States Patent
Kim et al.

(10) Patent No.: US 12,655,176 B2
(45) Date of Patent: Jun. 16, 2026

(54) SYSTEM AND METHOD FOR GENERATING A PROTEIN SEQUENCE

(71) Applicant: THE GOVERNING COUNCIL OF THE UNIVERSITY OF TORONTO, Toronto (CA)

(72) Inventors: Philip M. Kim, Toronto (CA); Alexey V. Strokach, Toronto (CA); David B. Romero, Etobicoke (CA); Carlos Corbi Verge, Toronto (CA); Alberto Perez Riba, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 1050 days.

(21) Appl. No.: 17/781,805

(22) PCT Filed: Dec. 4, 2020

(86) PCT No.: PCT/CA2020/051669
§ 371 (c)(1),
(2) Date: Jun. 2, 2022

(87) PCT Pub. No.: WO2021/108919
PCT Pub. Date: Jun. 10, 2021

(65) Prior Publication Data
US 2022/0372068 A1 Nov. 24, 2022

Related U.S. Application Data

(60) Provisional application No. 62/944,648, filed on Dec. 6, 2019.

(51) Int. Cl.
C07K 1/00 (2006.01)
G16B 15/20 (2019.01)
G16B 40/20 (2019.01)

(52) U.S. Cl.
CPC ................ *C07K 1/00* (2013.01); *G16B 15/20* (2019.02); *G16B 40/20* (2019.02)

(58) Field of Classification Search
CPC .......... C07K 1/00; G16B 15/20; G16B 40/20; G16B 20/50
See application file for complete search history.

(56) References Cited

U.S. PATENT DOCUMENTS

2003/0130797 A1* 7/2003 Skolnick ................ G16B 15/00
702/19
2003/0157487 A1* 8/2003 Gold .................... G01N 33/532
435/5

(Continued)

FOREIGN PATENT DOCUMENTS

WO WO-2020225693 A1 * 11/2020 ............. G06N 3/044

OTHER PUBLICATIONS

Bleicher L, Lemke N, Garratt RC. Using amino acid correlation and community detection algorithms to identify functional determinants in protein families. PLoS One. 2011;6(12):e27786. doi: 10.1371/journal.pone.0027786. Epub Dec. 20, 2011. PMID: 22205928; PMCID: PMC3243672. (Year: 2011).*

(Continued)

*Primary Examiner* — Sun M Li
(74) *Attorney, Agent, or Firm* — Marc Lampert; Bhole IP Law

(57) ABSTRACT

A method and system for generating a protein sequence is implemented using a computer-implemented neural network. An empty or partially filed sequence of node elements, representing amino acid positions of the protein sequence, and an edge index, having edge elements defining physical interaction between amino acid positions, are received. The computer-implemented neural network operates to determine enhanced edge attribute values for edge elements of the edge index and enhanced amino acid values for node (Continued)

elements of the sequence. Amino acid values are generated for elements of the partially filed sequence having missing values.

20 Claims, 15 Drawing Sheets

(56)                    References Cited

U.S. PATENT DOCUMENTS

| | | | | |
|---|---|---|---|---|
| 2011/0301331 A1* | 12/2011 | Glaser | .................... | G16B 15/00 |
| | | | | 435/254.2 |
| 2013/0303387 A1* | 11/2013 | Sander | .................. | G16B 15/00 |
| | | | | 703/11 |
| 2014/0221216 A1* | 8/2014 | Cope | ...................... | G16B 15/00 |
| | | | | 506/1 |
| 2018/0165412 A1* | 6/2018 | Frey | ........................ | G16B 20/20 |
| 2019/0018019 A1* | 1/2019 | Shan | ....................... | G16B 40/10 |
| 2020/0234788 A1* | 7/2020 | AlQuraishi | ............ | G16B 40/20 |
| 2022/0230710 A1* | 7/2022 | Amimeur | ............... | G06N 3/123 |
| 2022/0348999 A1* | 11/2022 | Tori | ................... | C12N 15/1093 |

OTHER PUBLICATIONS

Y. Du and C. Yan, "An Efficient Method for Discovering Functionally Important Motifs in a Group of Protein Structures," 2018 International Conference on Computational Science and Computational Intelligence (CSCI), Las Vegas, NV, USA, 2018, pp. 1345-1350, doi: 10.1109/CSCI46756.2018.00261. (Year: 2018).*

Creswell et al. Generative Adversarial Networks IEEE Signal Processing Magazine pp. 53-65 (Year: 2018) (Year: 2018).*

L. Liu et al., "Integrating Sequence and Network Information to Enhance Protein-Protein Interaction Prediction Using Graph Convolutional Networks," 2019 IEEE International Conference on Bioinformatics and Biomedicine (BIBM), San Diego, CA, USA, 2019, pp. 1762-1768, doi: 10.1109/BIBM47256.2019.8983330. (Year: 2019).*

D. Zhang and M. R. Kabuka, "Protein Family Classification with Multi-Layer Graph Convolutional Networks," 2018 IEEE International Conference on Bioinformatics and Biomedicine (BIBM), Madrid, Spain, 2018, pp. 2390-2393, doi: 10.1109/BIBM.2018.8621520. (Year: 2018).*

Ingraham et al., "Generative Models for Graph-Based Protein Design" Advances in Neural Information Processing Systems 32 (NeurIPS 2019), Mar. 27, 2019.

O'Connell, James et al. "SPIN2: Predicting sequence profiles from protein structures using deep neural networks." Proteins vol. 86,6 (2018): 629-633. doi:10.1002/prot.25489.

Chen et al., "To Improve Protein Sequence Profile Prediction through Image Captioning on Pairwise Residue Distance Map" J. Chem. Inf. Model. 2020, 60, 1, 391-399 Publication Date: Dec. 4, 2019 https://doi.org/10.1021/acs.icim.9b00438.

G. Zhou, J. Wang, X. Zhang and G. Yu, "DeepGOA: Predicting Gene Ontology Annotations of Proteins via Graph Convolutional Network," 2019 IEEE International Conference on Bioinformatics and Biomedicine (BIBM), 2019, pp. 1836-1841, doi: 10.1109/BIBM47256.2019.8983075.

Strokach et al., "Designing real novel proteins using deep graph neural networks" bioRxiv 868935; Dec. 10, 2019 doi:https://doi.org/10.1101/868935.

International Search Report and Written Opinion for Application No. PCT/CA2020/051669, mailed Jan. 14, 2021, 9 pages.

Bava, K Abdulla et al. "ProTherm, version 4.0: thermodynamic database for proteins and mutants." Nucleic acids research vol. 32, Database issue (2004): D120-1. doi:10.1093/nar/gkh082.

Bommarius, Andreas S, and Marietou F Paye. "Stabilizing biocatalysts." Chemical Society reviews vol. 42, 15 (2013): 6534-65. doi:10.1039/c3cs60137d.

Chevalier, A., Silva, DA., Rocklin, G. et al. Massively parallel de novo protein design for targeted therapeutics. Nature 550, 74-79 (2017). https://doi.org/10.1038/nature23912.

Dal Palu, A., Dovier, A. Fogolari, F. Constraint Logic Programming approach to protein structure prediction. BMC Bioinformatics 5, 186 (2004). https://doi.org/10.1186/1471-2105-5-186.

Dawson, Natalie L et al. "CATH: an expanded resource to predict protein function through structure and sequence." Nucleic acids research vol. 45,D1 (2017): D289-D295. doi:10.1093/nar/gkw1098.

Deller, Marc C et al. "Protein stability: a crystallographers perspective." Acta crystallographica. Section F, Structural biology communications vol. 72, Pt 2 (2016): 72-95.

Desmet, J., Maeyer, M., Hazes, B. et al. The dead-end elimination theorem and its use in protein side-chain positioning. Nature 356, 539-542 (1992). https://doi.org/10.1038/356539a0.

Fischman, Sharon, and Yanay Ofran. "Computational design of antibodies." Current opinion in structural biology vol. 51 (2018): 156-162. doi:10.1016/j.sbi.2018.04.0070.

Khan, Sofia, and Mauno Vihinen. "Performance of protein stability predictors." Human mutation vol. 31,6 (2010): 675-84. doi:10.1002/humu.21242.

Kocić et al., "An End-to-End Deep Neural Network for Autonomous Driving Designed for Embedded Automotive Platforms" Sensors 2019, 19(9), 2064.

Kroncke, Brett M et al. "Documentation of an Imperative to Improve Methods for Predicting Membrane Protein Stability." Biochemistry vol. 55,36 (2016): 5002-9. doi:10.1021/acs.biochem.6b00537.

Leach, A R, and A P Lemon. "Exploring the conformational space of protein side chains using dead-end elimination and the A* algorithm." Proteins vol. 33,2 (1998): 227-39.

Lewis, Tony E et al. "Gene3D: Extensive prediction of globular domains in proteins." Nucleic acids research vol. 46, D1 (2018): D435-D439. doi:10.1093/nar/gkx1069.

Li, Zhixiu et al. "Direct prediction of profiles of sequences compatible with a protein structure by neural networks with fragment-based local and energy-based nonlocal profiles." Proteins vol. 82, 10 (2014): 2565-73. doi:10.1002/prot.24620.

McGuffin, L J et al. "The PSIPRED protein structure prediction server." Bioinformatics (Oxford, England) vol. 16,4 (2000): 404-5. doi:10.1093/bioinformatics/16.4.404.

Palm et al., "Recurrent Relational Networks" Part of Advances in Neural Information Processing Systems 31 (NeurIPS 2018).

Park et al., "Simultaneous Optimization of Biomolecular Energy Functions on Features from Small Molecules and Macromolecules" J. Chem. Theory Comput. 2016, 12, 12, 6201-6212.

Prates et al., "Learning to Solve NP-Complete Problems: A Graph Neural Network for Decision TSP" vol. 33 No. 01: AAAI-19, IAAI-19, EAAI-20—Jul. 17, 2019.

Rocklin, Gabriel J et al. "Global analysis of protein folding using massively parallel design, synthesis, and testing." Science (New York, N.Y.) vol. 357,6347 (2017): 168-175. doi:10.1126/science.aan0693.

Schymkowitz, Joost et al. "The FoldX web server: an online force field." Nucleic acids research vol. 33,Web Server Issue (2005): W382-8. doi:10.1093/nar/gki387.

Silver, D., Schrittwieser, J., Simonyan, K. et al. "Mastering the game of Go without human knowledge." Nature 550, 354-359 (2017).

Simonis, H. "Models for Global Constraint Applications." Constraints 12, 63-92 (2007).

Sun MGF, Kim PM (2017) Data driven flexible backbone protein design. PLoS Comput Biol 13(8): e1005722.

Sun, Mark G F et al. "Protein engineering by highly parallel screening of computationally designed variants." Science advances vol. 2,7 e1600692. Jul. 20, 2016, doi:10.1126/sciadv.1600692.

Ullah, Abu Dayem, and Kathleen Steinhofel. "A hybrid approach to protein folding problem integrating constraint programming with local search." BMC bioinformatics vol. 11 Suppl 1,Suppl 1 S39. Jan. 18, 2010, doi:10.1186/1471-2105-11-S1-S39.

Wainberg et al. "Deep learning in biomedicine." Nature biotechnology vol. 36,9 (2018): 829-838. doi:10.1038/nbt.4233.

(56) References Cited

OTHER PUBLICATIONS

Wang, J., Cao, H., Zhang, J.Z.H. et al. Computational Protein Design with Deep Learning Neural Networks. Sci Rep 8, 6349 (2018). https://doi.org/10.1038/s41598-018-24760-x.

Witvliet et al., "ELASPIC web-server: proteome-wide structure-based prediction of mutation effects on protein stability and binding affinity." Bioinformatics, Vol.

Xu, Dong, and Yang Zhang. "Ab initio protein structure assembly using continuous structure fragments and optimized knowledge-based force field." Proteins vol. 80,7 (2012): 1715-35. doi:10.1002/prot.24065.

D. Shultis et al., Changing the Apoptosis Pathway through Evolutionary Protein Design. J. Mol. Biol. 431, 825-841 (2019), Elsevier.

D. K. Witvliet et al., ELASPIC web-server: proteome-wide structure-based prediction of mutation effects on protein stability and binding affinity. Bioinforma. Oxf. Engl. 32, 1589-1591 (2016), Oxford University Press.

* cited by examiner

SYSTEM AND METHOD FOR GENERATING A PROTEIN SEQUENCE

RELATED PATENT APPLICATION

The present application claims priority from U.S. provisional patent application No. 62/944,648, filed Dec. 6, 2019, and entitled "SYSTEM AND METHOD FOR GENERATING A PROTEIN SEQUENCE", the disclosure of which is hereby incorporated by reference in its entirety.

TECHNICAL FIELD

The technical field generally relates to system and method for generating a protein sequence using a trained neural network, and more particularly, for filling a partially filled sequence by modeling the sequence as a graph network and performing a graph convolution within the neural network.

BACKGROUND

Protein structure and function emerges from the specific geometric arrangement of their linear sequence of amino acids, commonly referred to as a fold. Engineering sequences to fold in a specific structure and function has a broad variety of uses, including academic research (1), industrial process engineering (2), and most notably, protein-based therapeutics, which are now a very important class of drugs (3, 4). Despite substantial advances, precisely designing sequences that fold into a predetermined shape (the "protein design" problem) remains difficult. For example, existing methods include limitations such as relatively low accuracy of current force fields, inability to sample more than a small portion of the search space and/or being labor intensive.

Thus, many challenges still exist in the design and generation of new protein sequences.

SUMMARY

The present description, according to one aspect, relates to a method for a method for generating a protein sequence, the method comprising:

receiving an empty or partially filled sequence of node elements, each node element of the sequence representing an amino acid position of the protein sequence and having an amino acid value chosen from one of a predetermined amino acid value and a missing value;

receiving an edge index of edge elements, each edge element of the edge index being associated to a respective pair of the node elements and having at least a presence value, a positive presence value indicating the presence of a physical interaction between the amino acid positions corresponding to the pair of node elements, the edge index thereby defining a desired fold structure of the protein sequence;

processing, by a computer-implemented neural network, a working copy of the partially filled sequence and the edge index to:

determine, for each given edge element of the edge index having a positive presence value, an enhanced edge attribute value set based on the amino acid values of the pair of node elements of the working copy sequence associated to the given edge element;

determine, for each given node element of the working copy sequence, an enhanced amino acid value based on the enhanced edge attribute value sets for every edge element having a positive presence value associated to the given node element; and for each given node element of the partially filled sequence having the missing value, determining a generated amino acid value based on the enhanced amino acid value corresponding to the given node element.

The present description, according to another aspect, relates to a system having at least one memory and at least one processor coupled to the memory. The processor is configured for:

receiving an empty or partially filled sequence of node elements, each node element of the sequence representing an amino acid position of the protein sequence and having an amino acid value chosen from one of a predetermined amino acid value and a missing value;

receiving an edge index of edge elements, each edge element of the edge index being associated to a respective pair of the node elements and having at least a presence value, a positive presence value indicating the presence of a physical interaction between the amino acid positions corresponding to the pair of node elements, the edge index thereby defining a desired fold structure of the protein sequence;

processing, by a computer-implemented neural network, a working copy of the partially filled sequence and the edge index to:

determine, for each given edge element of the edge index having a positive presence value, an enhanced edge attribute value set based on the amino acid values of the pair of node elements of the working copy sequence associated to the given edge element;

determine, for each given node element of the working copy sequence, an enhanced amino acid value based on the enhanced edge attribute value sets for every edge element having a positive presence value associated to the given node element; and for each given node element of the partially filled sequence having the missing value, determining a generated amino acid value based on the enhanced amino acid value corresponding to the given node element.

In some embodiments, the present description relates to a computer program product comprising a non-transitory storage medium having stored thereon computer-readable instructions, wherein the instructions when executed on a processor causes the processor to carry out the method according to various example embodiments described herein.

In some embodiments, the present description relates to a protein sequence generated by the method according to various example embodiments described herein.

In some embodiments, the present description relates to a nucleic acid sequence encoding the protein sequence according to various example embodiments described herein.

In some embodiments, the present description relates to an expression vector comprising the nucleic acid according to various example embodiments described herein.

In some embodiments, the present description relates to a host cell comprising the nucleic acid according to various example embodiments described herein.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, "protein" or "polypeptide", or any protein/polypeptide enzymes described herein, refers to any peptide-linked chain of amino acids, which may comprise any type of modification (e.g., chemical or post-translational modifications such as acetylation, phosphorylation, glycosylation, sulfatation, sumoylation, prenylation, ubiquitination, etc.), and is preferably a stable protein. For further clarity, protein/polypeptide/enzyme modifications are envisaged so long as the modification does not destroy the desired activity or stability.

As used herein, the term "stable" protein refers to a generated protein sequence comprising a stable structure (secondary and/or tertiary structure). In some embodiments, the protein is thermodynamically stable. In some embodiments, the protein stability may be determined by but not limited to X-ray crystallography, circular dichroism (CD), differential scanning calorimetry (DSC), absorbance (Abs), fluorescence (FI) (spectroscopy), nuclear magnetic resonance (NMR), gel filtration, isothermal calorimetry, proteolysis, interferometry (e.g. dual polarisation), predictive modeling programs, and light scattering. In some embodiments, a stable protein is not degraded in vitro or in vivo.

As used herein, the term "amino acid" refers to naturally occurring amino acids, or any isomers thereof. The term "residue" as it relates to a polypeptide refers to an amino acid. In some embodiments, an amino acid may refer to a synthetic amino acid.

As used herein, the term "mutations" refers to changes in the sequence of a wild-type nucleic acid (e.g. DNA or RNA) sequence or changes in the sequence of a wild-type polypeptide sequence. Such mutations may be point mutations such as transitions or transversions. The mutations may be deletions, insertions or duplications. A mutant or variant protein refers to the resulting mutated protein.

As used herein, the term "recombinant" in the context of enzymes and polypeptides described herein, refer to those produced via recombinant DNA technology. In some embodiments, a recombinant protein may be produced by said technology, wherein a DNA sequence encoding said protein may be expressed in an expression vector or a host cell, and wherein said DNA sequence is transcribed into RNA and further translated into said protein. Said protein may be modified post-translationally and further purified using traditional purification methods. In some embodiments, the recombinant enzymes and polypeptides described herein may be structurally different, or may be present in a form (e.g., concentration, or purity) that would not be found in nature.

DETAILED DESCRIPTION

Figure 1:
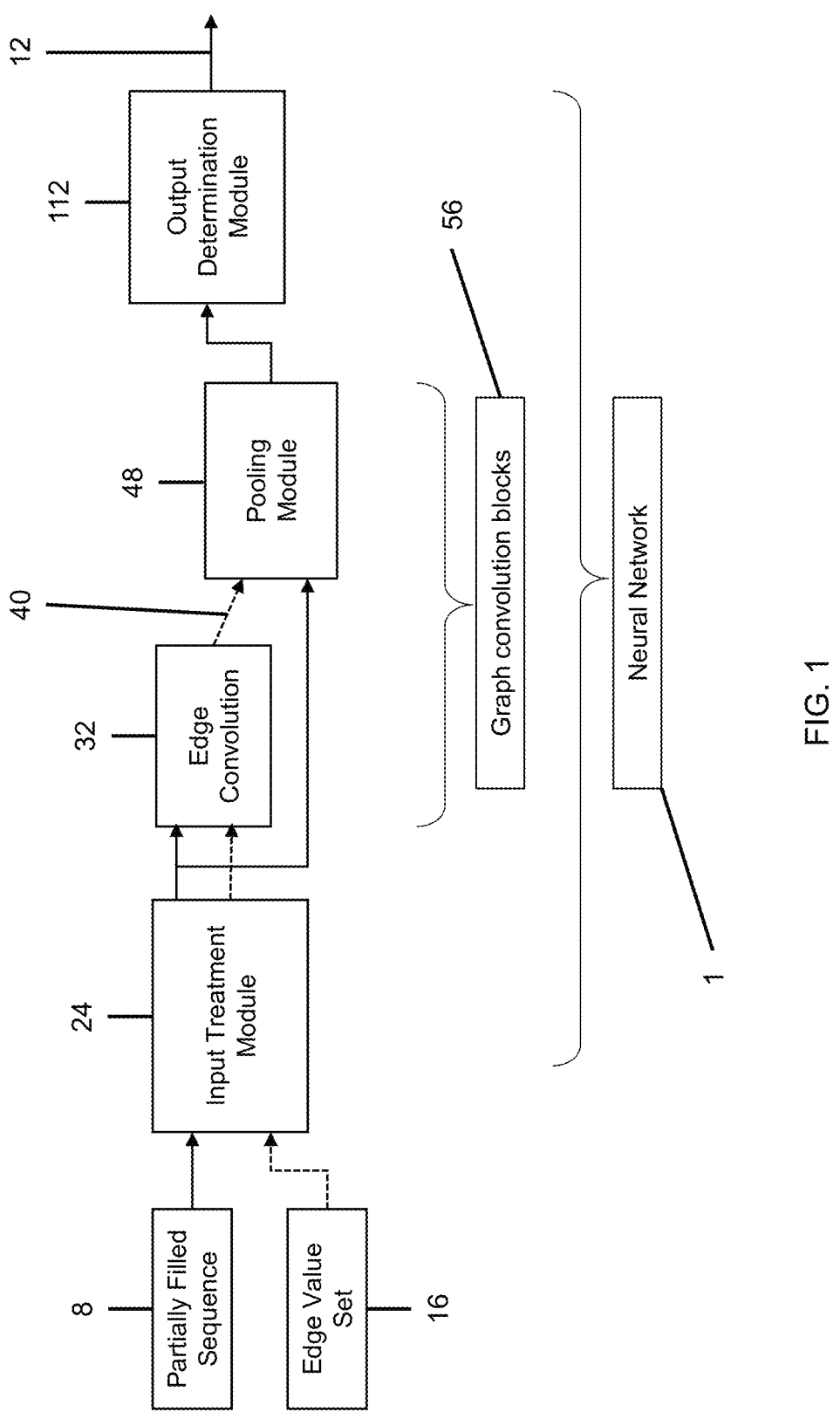
FIG. 1 illustrates a schematic diagram of the principal operational modules of a computer-implemented neural network system according to one example embodiment.

An Artificial Neural Network (ANN)—also referred to simply as a neural network is a computing system made up of a number of simple, highly interconnected processing elements (nodes/filters), which process information by their dynamic state response to external inputs. ANNs are processing devices (algorithms and/or hardware) that are loosely modeled after the neuronal structure of the mammalian cerebral cortex but on much smaller scales. A large ANN might have hundreds or thousands of processor units, whereas a mammalian brain has billions of neurons with a corresponding increase in magnitude of their overall interaction and emergent behavior. A feedforward neural network is an artificial neural network where connections between the units do not form a cycle.

Neural networks, that are designed to recognize patterns, such as in images and text. Neural networks are "trained" using labeled datasets or observed data, Neural networks are characterized by containing adaptive weights along paths between neurons that can be tuned by a learning algorithm that learns from observed data in order to improve the model.

Various embodiments described herein implements a neural network adapted for filling an initially empty or partially filled sequence. The neural network can be implemented using hardware elements, software elements or a combination thereof.

Software elements may be implemented in computer programs executing on programmable computers, each comprising at least one processor, a data storage system (including volatile and non-volatile memory and/or storage elements). For example, and without limitation, the programmable computer may be a programmable logic unit, a mainframe computer, server, and personal computer, cloud-based program or system, laptop, game console, cellular telephone, smartphone, or tablet device.

Each program is preferably implemented in a high-level procedural or object-oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

Furthermore, the system, processes and methods of the described embodiments are capable of being distributed in a computer program product comprising a computer readable medium that bears computer-usable instructions for one or more processors. The medium may be provided in various forms including one or more diskettes, compact disks, tapes, chips, wireline transmissions, satellite transmissions, internet transmission or downloadings, magnetic and electronic storage media, digital and analog signals, and the like. The computer-usable instructions may also be in various forms including compiled and non-compiled code.

Referring now to FIG. 1, therein illustrated is a schematic diagram of the principal operational modules of a computer-implemented neural network system 1 according to one example embodiment. The illustrated computer-implemented neural network system has already undergone training by machine learning and is in an operation ready state for filling a protein sequence. Various methods for training the neural network by machine learning are described elsewhere herein.

The protein-generation neural network 1 receives as inputs a partially filled amino acid sequence 8 and an edge value set 16.

The partially filled amino acid sequence 8 represents the input to the problem for which the solution is the generated protein sequence 12. The partially filled amino acid includes one or more amino acid positions that each have an undefined value (i.e. have a missing value). Upon applying methods and systems described herein to the partially filled amino acid sequence 8, the amino acid positions each having an undefined value are replaced by a generated amino acid value, thereby resulting in a generated amino acid. These generated amino acid values represent predictions of the values for such positions in order for the generated amino acid to have the desired protein structure.

The partially filled amino acid sequence 8 consists of an ordered sequence of node elements, wherein each node element of the sequence represents an amino acid position (ex: first amino acid, second amino acid . . . nth amino acid) within the protein sequence that is to be filed.

In a typical completed amino acid chain forming a protein sequence, each amino acid of the sequence has a respective amino acid value, which is one of 20 possible amino acid values (ex: Ala (A), Ile (I), Asp (D), Arg (R), etc.). The amino acid sequence 8 is partially filled in that at least some of node elements have undefined amino acid values (i.e. the value from the 20 possible amino acid values has not been defined). Accordingly, within the received partially filled amino acid sequence 8, each node element has a respective amino acid chosen from one of a predetermined amino acid value and a missing value. A predetermined amino acid value has already been defined and can have one of the 20 possible amino acid values. A node element having a missing value indicates that the amino acid value for that node element is undefined and is to be determined by the protein-generation neural network 1.

According to some example embodiments, at least some of the node elements of the partially filled protein sequence 8 have a predetermined amino acid value.

In some example scenarios, at least 20% of the node elements have a predetermined amino acid value.

In some example scenarios, at least 50% of the node elements have a predetermined amino acid value.

In some example scenarios, at least 80% of the node elements have a predetermined amino acid value.

In other example embodiments, less than 10% of the node elements have a predetermined amino acid value. In yet other example embodiments, all of the node elements have a missing value, such that a generated amino acid value needs to be determined for each of the amino acid positions of the input protein sequence 8.

The edge value set 16 includes at least an edge index of edge elements. The edge index acts as an adjacency matrix and defines those node elements of the partially filled sequence that have a relationship. More particularly, each element of the edge index 16 is associated to a respective pair of node elements of the partially filled sequence 8 and has a presence value. A positive presence value (ex: '1' bit) indicates the presence of a physical interaction between the amino acid positions corresponding to the node elements associated to that edge. It will be appreciated that a physical interaction between amino acids of a protein sequence will be present when amino acids are sufficiently close to one another, which is a function of the fold structure of the protein sequence. The physical interaction may also be caused and/or varied due to the respective charges of the amino acids. Accordingly, the edge index defines (ex: models in part) the desired fold structure of the protein sequence that is to be generated.

According to various example embodiments, pairs of amino acids (represented by pairs of node elements within the partially filed sequence 8) are considered to have a physical interaction if the distance between the amino acids within the Euclidean space are below a predetermined threshold. For example, the predetermined threshold is approximately 12 Angstrom. However, it will be understood that other distance threshold for determining the presence of a physical interaction between a pair of nodes can be chosen.

According to various example embodiments, the partially filled sequence comprises a sequence for a given protein fold. The given fold may be an alpha-helix or a beta-sheet, or any combination thereof. For example, a sequence comprising mainly alpha-helices, such as for serum albumin; sequences comprising mainly beta-sheets such as for immunoglobulin or a PDZ3 domain; and sequences comprising a combination of alpha-helices and beta-sheets, such as for alanine racemase, can be used as partially filled sequences, whereby the remainder of the amino acid values are generated.

According to various example embodiments, the partially filled sequence comprises a sequence for a protein, wherein certain amino acid values will be mutated to generate a mutant or variant of said protein. The mutations comprise additions, substitutions, or deletion of one or more amino acid values. In certain embodiments, such mutations may be scored according to resulting stability of the generated final sequence.

According to various example embodiments, the amino acid is any proteogenic amino acid or any isomer thereof.

It will be appreciated that the combination of the partially filled sequence 8 and the edge index 16 represents the protein sequence that is to be generated as a graph structure. Each node element of the partially filled sequence 8 corresponds to a node (or vertex) of the graph network and each element of the edge index having a positive presence value indicates pairs of nodes that are connected (also adjacent or neighbors).

Figure 2:
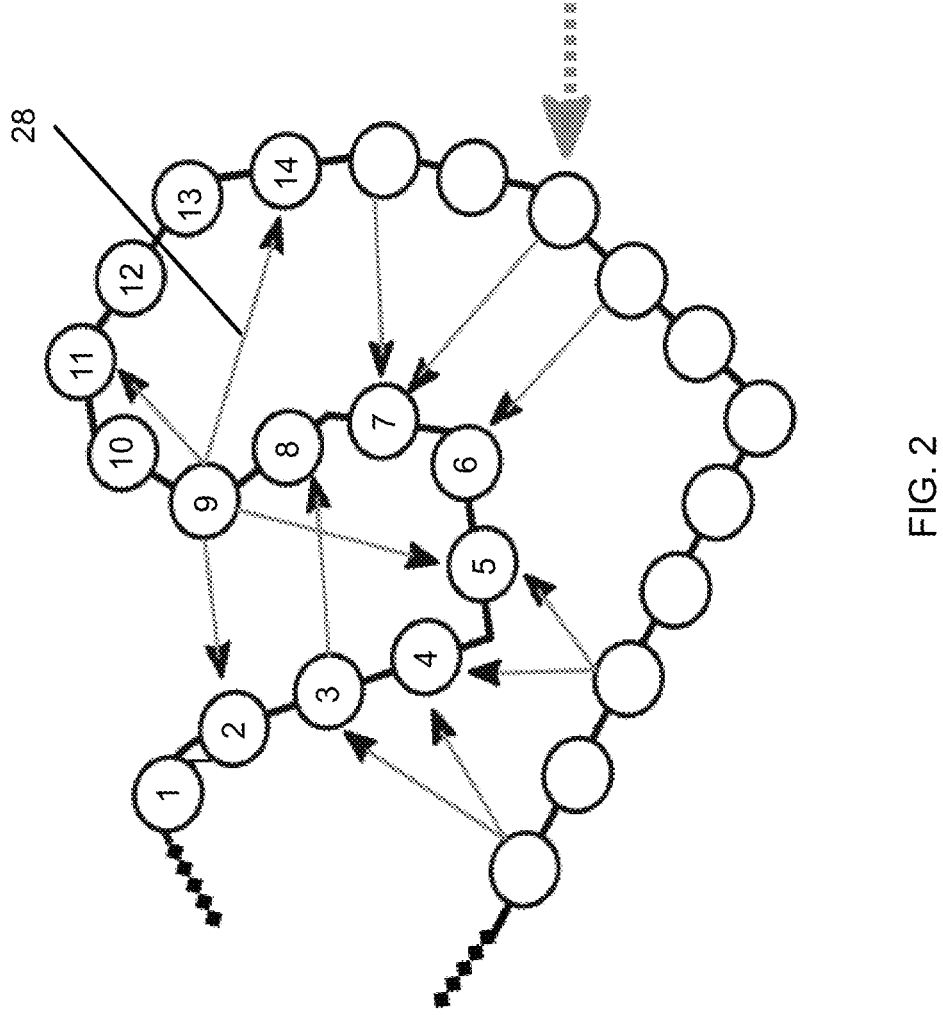
FIG. 2 illustrates a schematic diagram of a graph structure defined by the combination of partially filled amino acid sequences and edge index according to one example embodiment.

FIG. 2 illustrates a schematic diagram of a graph structure defined by the combination of the partially filled amino acid sequence 8 and the edge index of the edge value set 16. The circles represent node elements of the sequence, each node element's amino acid position being represented by its order in the connected chain of circles. Edge elements indicating a positive interaction between a pair of nodes are represented by the connection between the pair of nodes. It will be appreciated that there is an edge between each pair of mutually adjacent amino acid positions. Edge connections can also exist between non-adjacent amino acid positions.

According to various example embodiments, the edge value set 16 can include an edge attribute dataset. For each edge element of the index having a positive presence value, the edge attribute dataset defines a respective attribute value set that further defines at least one characteristic of the physical interaction between the amino acid positions corresponding to the node elements associated to that edge element. That is, in addition to indicating that two amino acid elements have a physical interaction, the corresponding attribute value set of the edge attribute dataset further defines at least one characteristic of that physical interaction.

The at least one characteristic of the physical interaction for a given pair of amino acid positions corresponding to a pair of node elements of the partially filled sequence 8 can include one or more of a Euclidian distance between the amino acid positions and/or a positional offset between the amino acid positions. It will be appreciated that other metrics, such as relative charge or orientation of the residues with respect to one another, may play a role in the physical interaction for a given pair of amino acids.

It will be appreciated that the edge attribute dataset can also act as the edge index. For example, instead of having a separate edge index that only includes presence values to indicate presence of physical interaction between pairs of nodes, the edge attribute value sets within the edge attribute dataset can also be used to indicate this presence of physical interaction. Accordingly, the edge index can be implicit within the edge attribute dataset.

Continuing with FIG. 1, the protein-generation neural network 1 includes an input treatment module 24 that applies one or more input treatment steps to the received partially filled sequence 8 and the edge value set 16. The received partially filled sequence 8 and the edge value set 16 may be treated separately within the input treatment module 16. The input treatment steps can include one or more steps known in the art for improving performance of the neural network system 1.

A working copy of the received partially filled sequence 8 (hereinafter "working copy sequence") can be fed into the protein-generation neural network 1. The working copy is a copy of the originally received partially filled sequence 8, whereby amino acid values of the node elements of the working copy can be updated one or more times within the protein-generation neural network 1.

According to one example embodiment, the working copy sequence is fed into an embedding submodule to embed all of the amino acid values of the sequence 8 into an embedding space having a predetermined dimensionality. The embedding space can have more than 100 dimensions, such as 128 dimensions. The embedded working copy sequence 8 can then be adjusted and/or scaled, such as using a batch normalization submodule. An activation function can then be applied to the normalized sequence prior to further processing within the neural network 1. The activation function can be a rectified linear unit (ReLU).

Similarly, according to one example embodiment, the edge value set 16 can also be treated by the input treatment module 24 where the edge value set 16 includes the edge attribute dataset defining at least one characteristic of the physical interactions between pairs of amino acid positions. The edge attribute dataset can also be fed into an embedding submodule to embed the edge attribute values into an embedding space having a predetermined dimensionality. For example, the edge embedding can be carried out in a 2-layer feed-forward network with 256 elements in the hidden layer). The embedding space of the edge value set 16 can also have more than 100 dimensions, such as 128 dimensions. The embedded edge attribute values can then be adjusted and/or scaled, such a using batch normalization submodule. An activation function can then be applied to the normalized sequence prior to further processing within the neural network 1. The activation function can be a rectified linear unit (ReLU).

The treated working copy sequence and the treated edge value set 16 is further fed as inputs to an edge convolution module 32. The edge convolution module 32 can be a subnetwork of the neural network system 1. In various example embodiment, the edge convolution module 32 is a trained multilayer perceptron (MLP). The edge convolution module 32 applies a type of convolution for each edge (as defined by the edge index of the edge dataset 16). The convolution for each edge determines an enhanced edge attribute value set based at least on the amino acid values of the pair of node elements of the working copy sequence associated to the given edge element. The amino acid values of the node elements can be the original amino acid values of the node elements or can be the enhanced amino acid values of the node elements, as described elsewhere herein. More particularly, for each given edge (i.e. for each edge element of the edge index having a positive presence value), the convolution module 32 receives as its inputs: 1) an edge attribute value set for the given edge; 2) the amino acid value (original or enhanced) of a first node connected to that edge (as defined by the edge index); and 3) the amino acid value (original or enhanced) of the other node connected to that edge (as defined by the edge index). It will be understood that according to example embodiments wherein the edge attribute value set is not initially provided, the edge attribute value set is not used as an input. An enhanced edge attribute value is determined and outputted for each edge element that indicates a positive presence of physical interaction between its connected nodes.

For example, in the example graph structure illustrated in FIG. 2, an edge 28 defines a positive presence of physical interaction between node elements corresponding to amino acid positions 9 and 14. The enhanced attribute value set for this edge is determined at least based on its own edge attributes, the amino acid value for the node element corresponding to position 9 and the amino acid value for the node element corresponding to position 14. For example, these values can be fed into the trained multi-layer perceptron.

In operation, the subnetwork of the edge convolution module 32 has already been trained using supervised learning. Accordingly, the weightings applied in the layers of the subnetwork (ex: the MLP) have already been determined during the supervised learning phase according to methods known in the art. It will be appreciated that the enhanced edge attribute value set for each edge element is enhanced in that it is endowed with information about the amino acid positions connected to it.

Continuing with FIG. 1, the enhanced edge attribute value sets 40 outputted by the edge convolution module 32 is fed as an input into the pooling module 48. The pooling module 48 is configured to determine, for each given node element of the working copy sequence, an enhanced amino acid value based on the enhanced edge attribute value sets for every edge element having a positive presence value associated to the given node element. In other words, for each amino acid position defined by the working copy sequence 8, the enhanced amino acid value for that amino acid position is determined based on the attribute values of each edge connected to that node element.

For example, in FIG. 2, the node element corresponding to amino acid position 9 is connected to six edges (edges connecting to amino acid positions 2, 5, 8, 10, 11 and 14). The enhanced attribute values of each of these six edges is used to determine the enhanced amino acid value for that node element.

According to one example embodiment, the enhanced amino acid value for a given node element is computed by applying a simple sum of the enhanced attribute values of the edges connected to that node.

According to another example embodiment, the pooling module 48 can be implemented as an attention block for applying a weighted sum, for a given node element, of the enhanced attribute values of edges connected to the given node.

It will be appreciated that the enhanced amino acid value for each node element is enhanced in that it is endowed with information about the edges connected to it. Furthermore, since each enhanced amino acid value is also endowed with information of its neighboring nodes, the enhanced amino acid value is also endowed with information about its neighboring nodes.

The combination of the edge convolution module 32 and the pooling module 48 forms a graph convolution block 56 of the neural network system 1. As described, the enhanced amino acid values outputted by the pooling module 48, and thereby the graph convolution block 56, is determined from a kind of convolution of their connected edge attribute values and neighboring node values.

According to various example embodiments, the protein generation neural network system 1 can include a plurality of repeated graph convolution blocks 56 wherein the working copy sequence having enhanced amino acid values and the edge attribute dataset having the enhanced edge attribute values determined in a preceding one of the graph convolution blocks 56 is provided as inputs to a subsequent one of the graph convolution blocks 56. Within each graph convolution block 56, the outputted enhanced amino acid value calculated for a given node element of the working copy sequence can replace the existing (inputted) amino acid value for that node element. It will be appreciated that the inputted amino acid values within the first graph convolution block 56 is the original amino acid values (contained within the working copy sequence) of the received partially filled sequence 8 as treated by the input treatment module 24.

Similarly, within each graph convolution block 56, the outputted enhanced edge attribute value set calculated for a given edge element can replace the existing (inputted) amino acid value for that edge element. It will be appreciated that the inputted edge attribute value sets within the first graph convolution block 56 is the original edge attribute dataset 16 as treated or an empty dataset (if no edge attribute dataset is initially received).

According to various example embodiments, the repeated graph convolution blocks 56 are residual blocks. Accordingly, within each given repeated graph convolution block/residual block 56, the enhanced amino acid values determined by the given block 56 are added to the corresponding amino acid values inputted to the given block (ex: original treated sequence 8 or enhanced amino acid values from a preceding block). Similarly, within each given repeated graph convolution block/residual block 56 the enhanced edge attribute value sets determined by the given block 56 are added to the corresponding edge attribute value sets inputted to the given block (ex: original edge attribute dataset or enhanced edge attribute value sets from a preceding block).

According to one example embodiment, the graph convolution block 56 includes at least 4 residual blocks. For example, the graph convolution block 56 can include 16 repeated residual blocks.

It will be appreciated that having a plurality of repeated graph convolution blocks, such as repeated residual blocks, allows the determined enhanced edge attributed value sets and the determined enhanced node attribute value sets to be endowed with information of its immediate neighbours (connected over one edge distance) as well as its neighbours that are further out (two or more edges away). Of course, this also allows for a deeper learning of information pertaining to relationships of amino acid values of protein structures.

Figure 3:
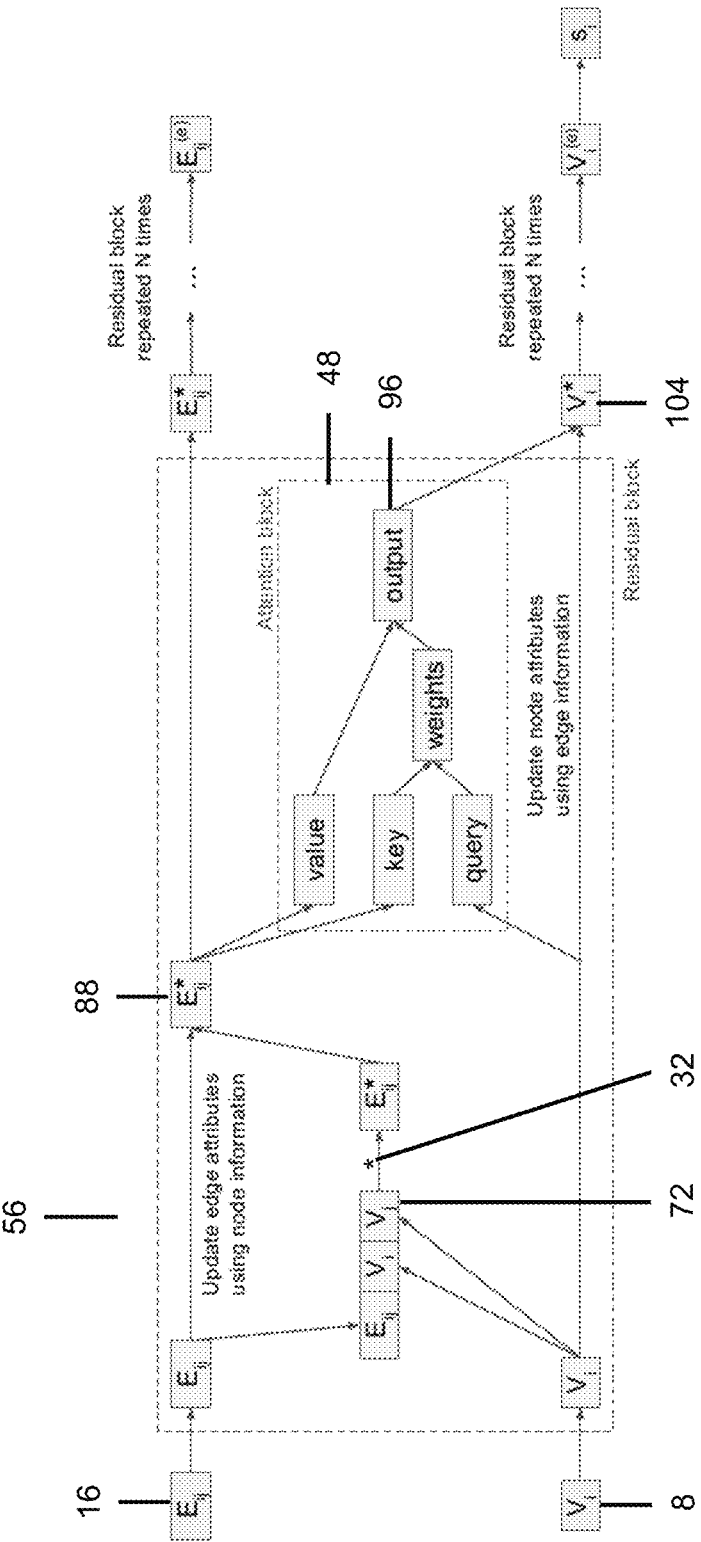
FIG. 3 illustrates a schematic diagram of one detailed residual block according to one example embodiment.

Referring now to FIG. 3, therein illustrated is a schematic diagram of one detailed residual block according to one example embodiment. It will be appreciated that the illustrated residual block includes an attention block as a pooling module 48, but that in other example embodiments another pooling method, such as a simple sum, can be used.

As described elsewhere herein, the residual block 56 receives as its inputs the working copy of the partially filled sequence 8 and the edge value set 16, the latter which can include the edge index and the edge attribute dataset.

For each edge element having a positive presence value, the edge attribute value set is combined with its connected node element amino acid values. For example, the edge attribute value set and its associated amino acid values can be concatenated to form a vector 72. This vector 72 is then fed as an input into the edge convolution 32, which can be implemented as a MLP, to determine the intermediate attribute value set 80 for the given edge element. The intermediate attribute value set 80 is added to the inputted attribute value set to obtain the enhanced edge attribute value set E* 88. The enhanced edge attribute value set E* 88 is determined for every one of the edge elements.

Then for each node element of the working copy sequence 8, the enhanced attribute value set E* 88 is inputted into the attention block/pooling module 48 as the value and key inputs of the attention block, and the amino acid value for the given node element is inputted as the query input of the attention block. The appropriate weights are applied to obtain the weighted output, which is an intermediate amino acid value 96 for the given node element. The intermediate amino acid value 96 is added to the inputted amino acid value to form the enhanced amino acid value V* 104 for the given node element. The enhanced amino acid value V* 104 can replace the corresponding existing amino acid value within the working copy of the sequence 8.

The enhanced amino acid values 104 and enhanced edge attribute value sets 88 are fed as inputs into a subsequent residual block 56 over the plurality of repeated subsequent residual blocks 56.

Some treatment can be applied to one or more of the intermediate edge attribute value set, the enhanced edge attribute value set, the intermediate amino acid value and the enhanced amino acid value. Each of the intermediate edge attribute value sets and the intermediate enhanced amino acid values can be normalized (ex: by applying a batch normalization). Furthermore, an activation function (ex: another ReLu) can be applied to each of the enhanced edge attribute value sets and enhanced amino acid values prior to being inputted into the next graph convolution block 56 (ex: residual block) within the repeated blocks.

Returning to FIG. 1, the protein generation neural network system 1 further includes an output determination module 112. The output determination module 112 receives as its input the working copy sequence having the enhanced amino acid values that is outputted by the graph convolution block 56. Where the graph convolution block 56 includes a plurality of repeated blocks, such as a plurality of repeated residual blocks, the working copy sequence generated by the last block in the chain is outputted from the graph convolution block 56 and is received as an input of the output determination module 112.

The output determination module 112 is operable to determine, for each given node element of the originally received partially filled sequence having the missing value, a generated amino acid value to replace the missing value. For each given node element of the originally received sequence 8 having the missing value, the generated amino acid value is determined based on the enhanced amino acid value of the working copy sequence 104 corresponding to that node element. For example, for a node element of the originally received partially filled sequence 8 associated to a given amino acid position, the enhanced amino acid value associated to the same amino acid position within the working copy sequence 104 is used to determine the generated amino acid value for that position.

A completely filled protein sequence 12 is formed from the originally received partially filled sequence 8 by keeping the value of the node elements having the predetermined amino acid values of the and node elements and by replacing the values of node elements having missing values by their respective generated amino acid values as determined by the output determination module 112.

For a given node element of the originally received partially filled sequence having a missing value, its generated amino acid value is determined by selecting the one value out of 20 possible amino acid value that has the probability as determined based on the corresponding enhanced amino acid value.

According to one example embodiment in which the amino acid values of the node elements of working copy of the protein sequence inputted into input treatment module 24 are each embedded to an embedding space of a particular dimensionality, the enhanced amino acid values will be vectors having the same dimensionality. Within the output determination module 112, a given enhanced amino acid value can be remapped back to the base dimensional space having a dimensionality corresponding to the number of possible amino acid values (i.e. a 20-dimensional space). This mapping can be carried out in a linear layer implemented within the output determination module. The 20-dimension outputs from the linear layer can be passed through a softmax activation function in order to convert the mapped enhanced amino acid value into a probability distribution for the 20 possible amino acid values, each possible amino acid value having a respective probability metric. The possible amino acid value having the highest probability metric is then selected as the generated amino acid value for the given node element corresponding to the given enhanced amino acid value.

The determination of the generated amino acid values for those node elements of the partially filled sequence having a missing value can be carried out in a one-shot generation process according to one example embodiment. According to this one-shot generation process, the partially filled protein sequence 8 is passed through the neural network only once (i.e. only one iteration). Within this single iteration, for each node element having a missing value, the possible amino acid value (out of 20 possible values) having the highest probability metric as determined within the output determination module 112 is selected as the generated amino acid value for that node element. The node elements having the missing values are assigned their respective generated amino acid value (thereby replacing the missing value), and this protein sequence is outputted as the final solution.

Alternatively, the determination of the generated amino acid values for those nodes elements of the partially filled sequence having a missing value can be carried out in an incremental generation process according another example embodiment. According to the incremental generation process, the partially filled protein sequence 8 is passed through the neural network system 1 over a plurality of iterations. Within each iteration, a subset of the node elements having missing values will have their amino acid value replaced by their respective generated amino acid value while the other node elements keep the missing value. This causes each iteration to output an intermediate partially filled sequence that still contains node elements having missing values. The total number of such node elements having missing values in the outputted intermediate sequence is less than the number of such node elements having missing values that was inputted into the neural network system 1 at the beginning of the iteration. This intermediate sequence outputted in the current sequence is provided as the input partially filled sequence for the subsequent iteration. Accordingly, a plurality of intermediate partially filled sequences are generated (1 intermediate sequence for each iteration) until all of the node element have either a predetermined amino acid value or a generated amino acid value (i.e. all node elements having a missing value have their value replaced by the generated amino acid value).

According to one example embodiment, the incremental generation process can proceed by determining only one generated amino acid value per iteration (i.e. only one node element having a missing value has its value replaced by a generated amino acid value per iteration). Within this embodiment, a generated amino acid value is still determined for each node element based on the possible amino acid value having the highest probability for each node element (ex: at position 1, D has a 0.65 probability; at position 3, R has a 0.84 probability; at position 7, T has a 0.58 probability . . . ). Then for all of the node elements, the node element associated to a generated amino acid value having the highest probability versus the probability of all other node elements (in the above example, position 3 has the highest probability at 0.84) is selected as the node element that will have its missing value replaced by its generated amino acid value. The intermediate partially filled sequence having this modified node element is inputted in the next iteration.

According to another example embodiment, a plurality of highly-probable solutions (i.e. a plurality of generated protein sequences) can be generated in parallel. This method proceeds similarly to an A* search. It is proposed that this achieves a compromise between the accuracy provided by an exhaustive breadth-first search and the speed provided by the greedy search. Within this embodiment, a generated amino acid value is still determined for each node element based on the possible amino acid value having the highest probability for each node element (ex: at position 1, D has a 0.65 probability; at position 3, R has a 0.84 probability; at position 7, T has a 0.58 probability . . . ). Then for all of the node elements, the node element associated to a generated amino acid value having the highest probability versus the probability of all other node elements (in the above example, position 3 has the highest probability at 0.84) is selected as the node element that will have its missing value replaced by its generated amino acid value. However, instead of only selecting the generated amino acid value having the highest probability, all generated amino acid values having a probability metric that exceeds a predetermined threshold is kept (ex: for position 3, R has a probability of 0.84, Y has a probability of 0.24 and Q has a probability of 0.15—all three amino acid values are kept because they exceed a predetermined threshold of 0.05). In this case, an intermediate partially filled sequence is generated for each of the amino acid values that has the highest probability metric (in the above example, three intermediate partially filled sequences are generated). These generated intermediates partially filled sequences are added to a priority queue to determine which of the sequences are to be passed on as input in the next iteration.

Figure 4:
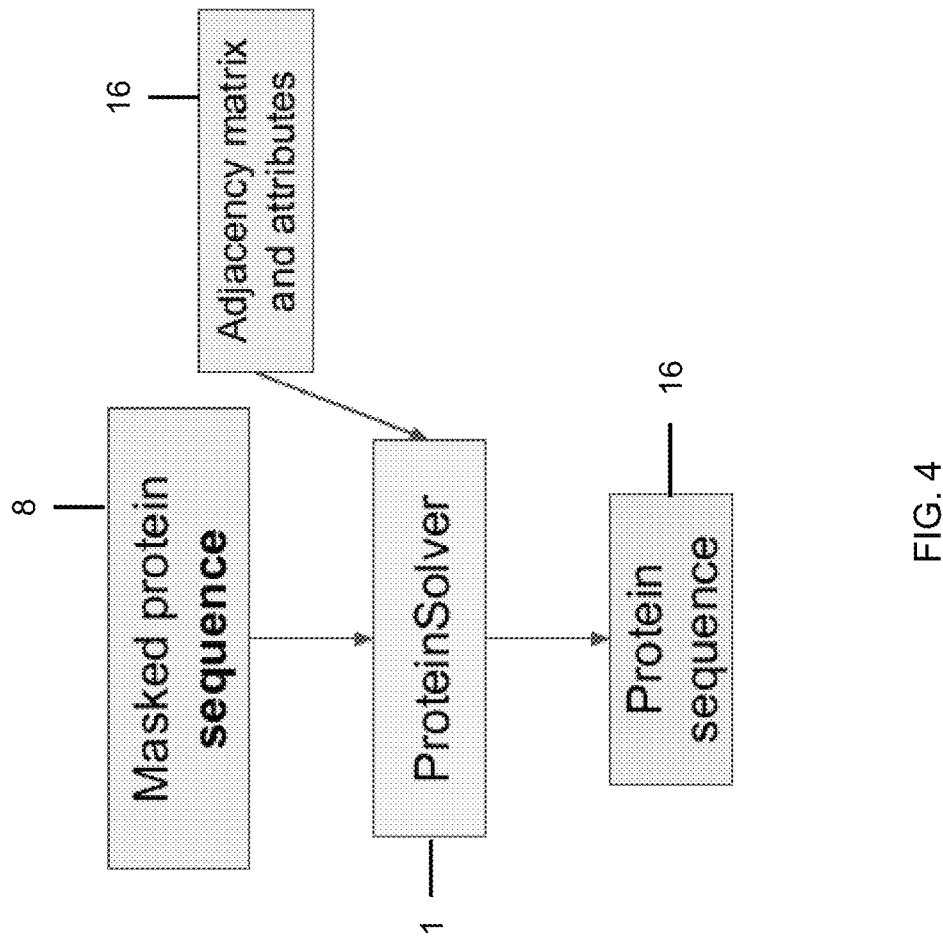
FIG. 4 illustrates a simplified schematic diagram of the protein generation neural network system according to one example embodiment.

Referring now to FIG. 4, therein illustrates a simplified schematic diagram of the protein-generation neural network system according to one example embodiment. As described elsewhere herein, the partially filled protein sequence 8 having masked amino acid values (i.e. having amino acid values defined as missing values) and the edge value set 16 (which may include edge index and edge attribute dataset) are received as inputs. These inputs are fed into the protein-generation neural network system 1 as described herein according to various example embodiments (nicknamed "Protein Solver"). One or more generated protein sequences 120 are outputted.

Figure 5:
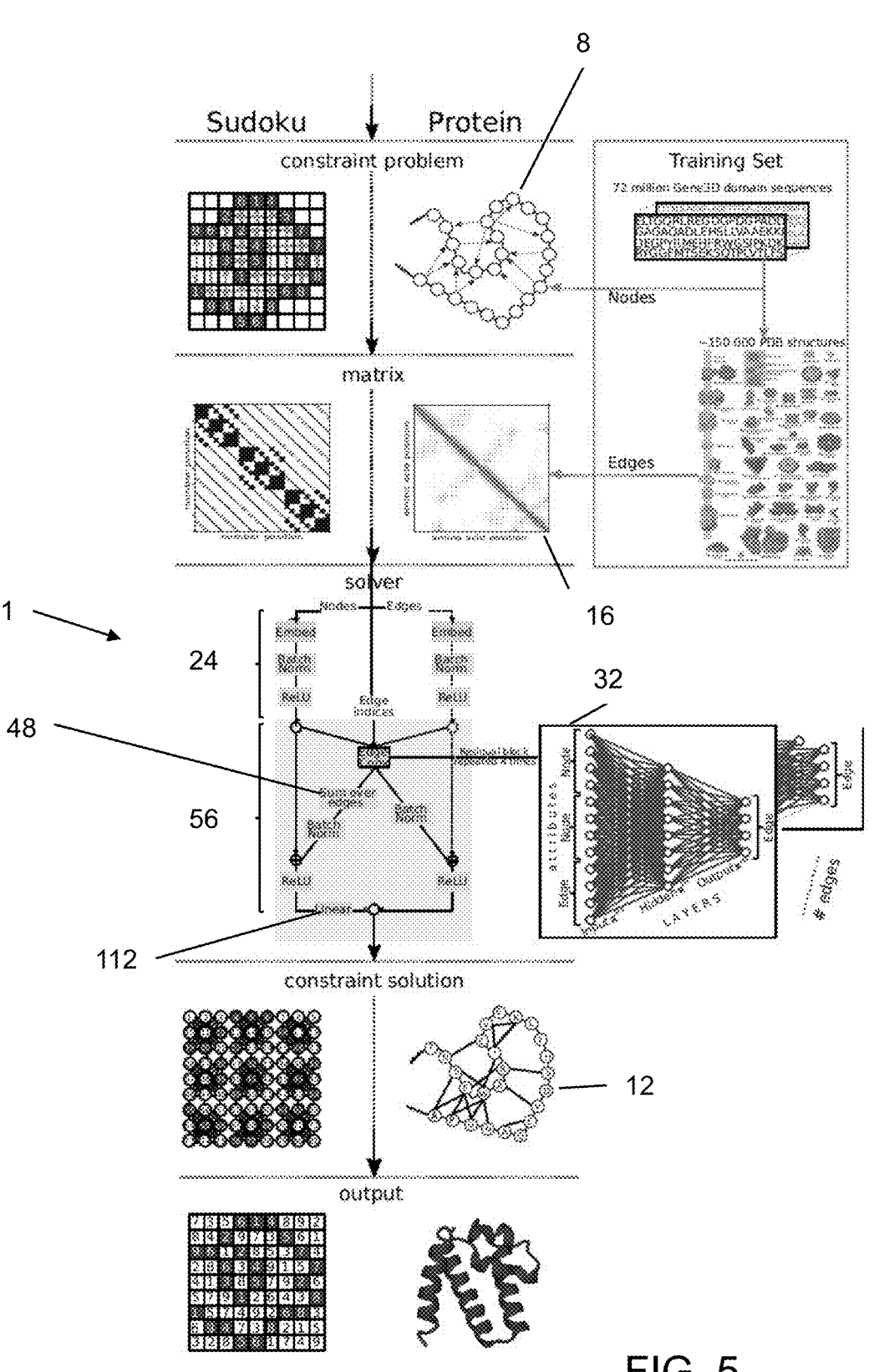
FIG. 5 illustrates a detailed schematic diagram of the neural network system according to one example embodiment.

Referring now to FIG. 5, therein illustrated is a detailed schematic diagram of the neural network system 1 according to one example embodiment. As described in the Experimentation and Examples section hereinbelow, the problem of generating a protein sequence from an initially partially filled sequence can be characterized as a constraint satisfaction problem that is analogous to solving a Sudoku puzzle problem. As further described, the architecture of the neural network system 1 can be initially designed for solving a Sudoku puzzle problem and then applied for the problem of generating protein sequences. Accordingly, as illustrated in FIG. 5, the architecture of the neural network system 1 can be applied to both a Sudoku puzzle problem and a protein generation sequence according to some example embodiments. However, in other example embodiments, the architecture can be specifically adapted for the problem of generating protein sequences.

Continuing with FIG. 5, the inputs are the partially filled protein sequence 8 and the edge value set 16. In the input treatment module 24, each of the working copy of the partially filled protein sequence and the edge value set are treated before further processing. For example, and as illustrated, each input is passed through a respective embedding process, a batch normalization process and a ReLu activation function. As described elsewhere herein, the amino acid values of the working copy sequence and the edge value sets are inputted into the edge convolution module 32, wherein for each edge element, an enhanced edge attribute value set is determined based on the amino acid values of its neighboring node elements and (optionally) its own attribute value set. In the illustrated example, the enhanced edge attribute value set is determined using its respective MLP 32.

The enhanced edge attribute value set is passed through another batch normalization process before being summed with its prior edge attribute value set, thereby forming a residual block. The summed enhanced edge attribute value is passed through another activation function (ReLu) prior to being inputted into a subsequent residual block.

For each node element, the outputted enhanced edge attribute value sets of its connected edges are also inputted into the pooling module 48, whereby the pooled sum becomes an enhanced amino acid value for the node element. The enhanced amino acid value is passed through another batch normalization process before being summed with its prior amino acid value, thereby also forming a residual block. The summed enhanced edge attribute value is passed through another activation function (ReLu) prior to being inputted into a subsequent residual block.

The enhanced amino acid value outputted from the final residual block is then inputted into the output determination module 112, which can include a linear layer to determine a respective generated amino acid value for each node element of the original partially filled protein sequence 8. This results in solving the constraint satisfaction problem and outputting a fully generated protein sequence 12.

Figure 6:
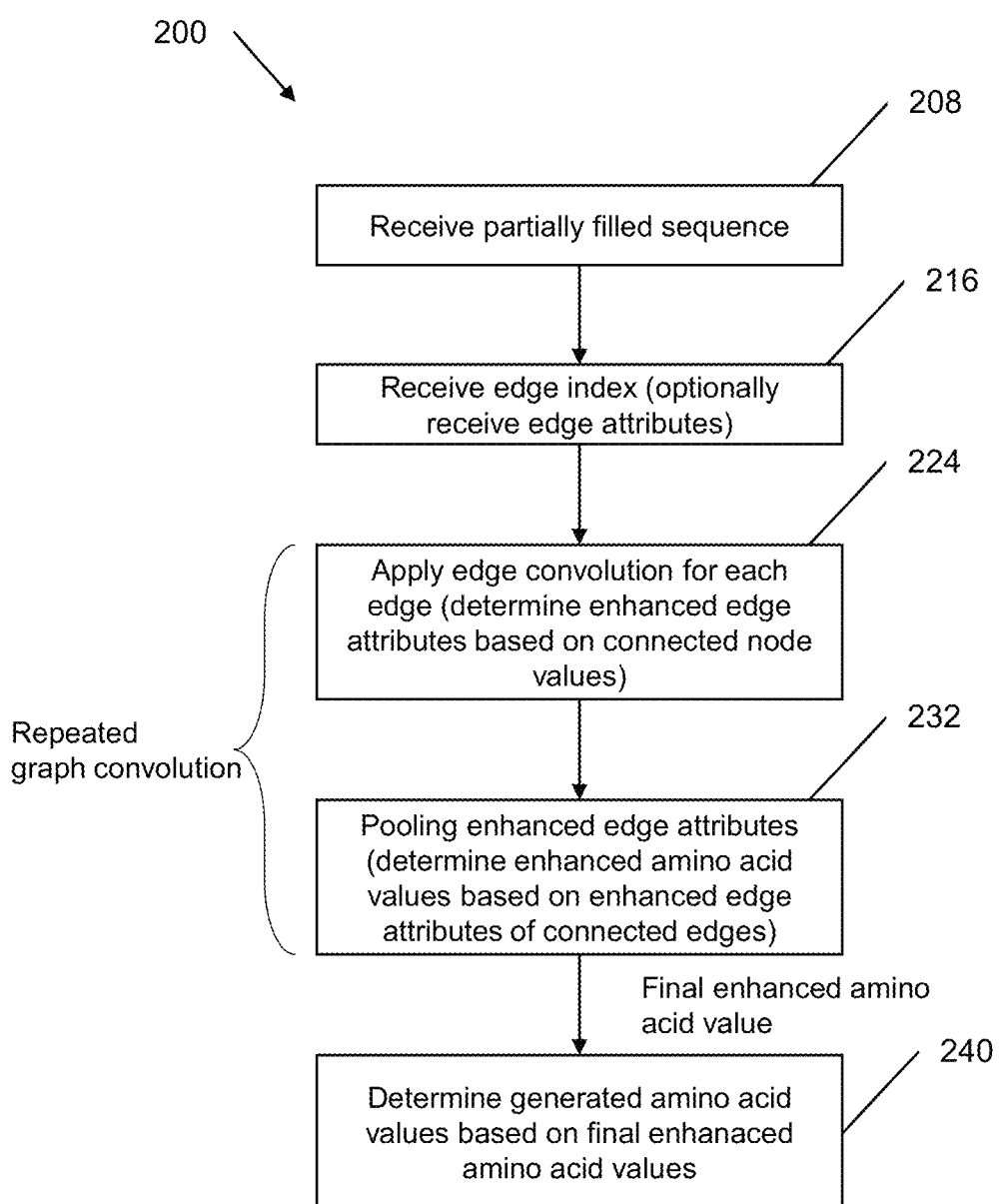
FIG. 6 illustrates a flowchart showing the operational steps of a computer-implemented method for generating a protein sequence according to one example embodiment.

Referring now to FIG. 6, therein illustrated is a flowchart showing the operational steps of a computer-implemented method 200 for generating a protein sequence according to one example embodiment.

At step 208, the partially filled protein sequence 8 is received.

At step 216, the edge value set 16 is received.

At step 224, an edge convolution is performed for each edge element having a positive presence value. As described elsewhere herein, an enhanced edge attribute value set is determined based on the amino acid values of the pair of nodes associated to that edge (i.e. connected to that edge). The enhanced edge attribute value set can be determined by feeding the amino acid values and edge attributes through a MLP trained for that edge.

At step 232, for each node element of a working copy sequence, the enhanced edge attribute value sets of the edge elements having a positive presence value associated to the node element (i.e. connected to the node) are pooled. This can be performed using simple sum of the enhanced edge attribute value sets or a weighted sum thereof. This determines an enhanced amino acid value for the given node element.

As described elsewhere herein, steps 224 and 232 form a graph convolution block, wherein the steps 224 and 232 are repeated a plurality of times over a plurality of graph convolution blocks 56, such as residual blocks. The last block outputs a final enhanced amino acid value.

At step 240, for each node element of the original partially filled sequence having the missing value, a generated amino acid value is determined based on its corresponding final enhanced amino acid value. The values of node elements within the original sequence initially having the missing value are then replaced by their respective generated amino acid value, thereby obtaining the fully generated protein sequence 12.

Training the Neural Network

During a training phase, the neural network system 1 is trained by a applying supervised machine learning. The learning is carried out using an annotated training dataset of known protein sequences.

At least one database of known protein sequences is initially identified. The database contains known protein sequences for which both the sequence of amino acid values and the physical structures of the sequences are defined.

The initial training set is prepared by generating a plurality of protein sequence entries from the known database, with each entry having an amino acid sequence each having a respective defined amino acid value and an edge value set. The edge value set can be extracted from the physical structure information contained in the protein sequence database. The edge value set can include an edge index indicating pairs of amino acid positions having a physical interaction (ex: having a distance below a predetermined distance threshold, such as 12 Angstroms). The edge value set can also include edge attribute dataset defining characteristics of the physical interaction between pairs of amino acid positions.

The annotated training dataset is then generated from the initial training set by further preparing an input subset and a target subset. Another subset can be set aside as the validation subset. The input subset is prepared by taking each protein sequence and masking a plurality of the amino acid values within the protein sequence, while the remainder of the amino acid values remain unmasked. The masking can be carried out by setting those amino acid values that are to be masked to have a missing value.

A copy of the initial training set having the fully non-masked amino acid values is kept as a target subset. Over 72 million sequences from the UniParc database were used for which a structural template could be found in the PDB. Structural templates have at least 30% sequence identity with the query sequences, which is an acceptable threshold for sequences that are likely to fold into a similar three-dimensional shape.

The neural network system 1 having the architecture described herein according to various example embodiments is provided in its untrained state. It is then trained by machine learning using the input subset and the target subset. More particularly, the neural network system 1 is trained so that for the protein sequences of the input subset having masked amino acid values, the neural network system 1 is configured to make a prediction of generated amino acid values that match the corresponding non-masked amino acid values of the target subset.

During training, parameters of the neural network system 1 are adjusted to reduce the differences between i) the predictions of the generated amino acid values for those position elements having masked values and ii) the corresponding non-masked amino acid values of the target set. This reduction of the difference can be carried out to minimize the cross-entropy-loss between the predictions of the generated amino acid values as determined by the neural network system applied to the input subset and their corresponding non-masked amino acid values in the target subset. The adjustment of parameters of the neural network system 1 during training thereof can be carried out according to various examples known in the art, such as using gradient descent, for example by applying backpropagation.

According to various examples, methods and systems described herein may be used in an application for generating an amino acid sequence. Various embodiments can be applied for generating a complete or partial amino acid sequence starting from an empty or partially filled sequence. According to various embodiments, the partially filled sequence comprises a sequence for a given protein fold. The given fold may be an alpha-helix or a beta-sheet, or any combination thereof. For example, a sequence comprising mainly alpha-helices, such as for serum albumin; sequences comprising mainly beta-sheets such as for immunoglobulin or a PDZ3 domain; and sequences comprising a combination of alpha-helices and beta-sheets, such as for alanine race-mase, can be used as partially filled sequences, whereby the remainder of the amino acid values are generated. According to various embodiments, the partially filled sequence comprises a sequence for a protein, wherein certain amino acid values will be mutated to generate a mutant or variant of said protein. The mutations comprise additions, substitutions, or deletion of one or more amino acid values. In certain embodiments, such mutations may be scored according to resulting stability of the generated final sequence.

According to various examples, methods and systems described herein may be used in an application for determining the stability of an amino acid sequence.

According to various, examples, methods, and systems described herein may be used in application for designing a novel, mutant, or variant protein, said examples, methods, and systems comprising generating an amino acid sequence and determining its stability for the purification and use of said protein.

According to various embodiments, the present description relates to a protein sequence generated by the methods and systems described herein. According to some embodiments, the present description relates to a nucleic acid sequence encoding the protein sequence generated by the methods and systems described herein. According to some embodiments, the present description relates to an expression vector comprising the nucleic acid encoding the protein sequence generated by the methods and systems described herein. According to some embodiments, the present description relates to a host cell comprising the expression vector or nucleic acid encoding the protein sequence generated by the methods and systems described herein.

According to various embodiments, the amino acid is any proteogenic amino acid or any isomer thereof.

Experimentation and Examples

It should be understood that the examples, neural networks, amino acids sequences, edge attributes and any other experimental parameters provided in the "Experimentation and Examples" section below are provided for illustrative purposes only and should be construed as limiting the methods and systems for filling a protein sequence of the present description or of the appended claims.

Designing a sequence from scratch to adopt a desired structure (referred to as the "inverse folding" or "protein design" problem) remains a very challenging task. Conventionally, a sampling technique such as Markov-chain Monte Carlo is used to generate a sequence optimized with respect to a force-field or statistical potential (4-6). Limitations include the relatively low accuracy of current force fields (7, 8) and the inability to sample more than a miniscule portion of the vast search space (sequence space size is $20^N$, N being the number of residues). While there have been successful approaches that screen many thousands of individual designs using in vitro selection (9, 10), these remain reliant on relatively labor-intensive experiments.

The methods and systems described herein provide a deep graph neural network, nicknamed Protein Solver, to accurately solve protein design phrased as a constraint satisfaction problem (CSP). To sidestep the considerable issue of optimizing the network architecture, first a network that is accurately able to solve the related and straightforward problem of Sudoku puzzles was develop. Recognizing that each protein design CSP has many solutions, this network was trained on millions of real protein sequences corresponding to thousands of protein structures. Experimentation shows that the method rapidly designs sequences with high accuracy, and this was confirmed using a variety of in silico and in vitro techniques to show that designed proteins indeed adopt the predetermined structures.

It was observed that filling a specific target structure with a new sequence can be formulated as a constraint satisfaction problem (CSP) where the goal is to assign amino acid labels to residues in a polymer chain such that the forces between interaction amino acids are favorable and compatible with the fold. To overcome previous difficulties with phrasing protein design as a CSP (11, 12), rules governing constraints are elucidated using deep learning. Such methods have been applied to a vast diversity of fields with impressive results (13-15), partly because they can infer hitherto hidden patterns from sufficiently large training sets. For proteins, the set of different protein folds is only modestly large with a few thousand superfamilies in CATH (16). Indeed, previous attempts at using deep learning approaches for protein design used structural features and thus only trained on relatively small datasets and achieved moderate accuracy (17, 18). However, the number of sequences that share these structural templates is many orders of magnitude larger (about 70,000,000 sequences map to the CATH superfamilies), reflecting the fact that the protein design problem is inherently underdetermined with a relatively large solution space. Thus, a suitable deep neural network trained on these sequence-structure relationships could potentially outperform previous models to solve the protein design problem.

The adjacency matrix is commonly used to represent protein folds; it is an N×N matrix consisting of the distances (in Angstrom) between residues which are spatially close and thus interacting (a distance threshold of 12 Angstrom is used as the cut-off for interaction); such pairs of residues are subject to constraints (e.g., in such pairs, two positive charges are usually not well tolerated). A given protein structure corresponding to one distance matrix can be formed by many different homologous sequences; these sequences all satisfy the constraints imposed. Such solutions to the constraint satisfaction problem are given by evolution and are available in sequence repositories such as Pfam or Gene3D (19). While the rules for this CSP for any specific fold are easily found by simply comparing sequences from one of such repositories and can be given as position weight matrices (PWMs), often represented as sequence logos, it has thus far not been possible to deduce general rules—those that would connect any given fold or adjacency matrix with a set of sequences. As described elsewhere herein, a graph neural network to elucidate these rules. The graph in this case is made up of nodes (corresponding to amino acids) with edges being the spatial interactions between amino acids that are represented in the distance matrix. The edges thus represent the constraints that are imposed on the node properties (amino acid types).

As there had been relatively little work in using graph neural networks to solve CSPs (20, 21), it was quite difficult to find an optimal network architecture for this relatively complex problem. Hence, a first graph neural network model was engineered and optimized to solve the related and well-defined problem of Sudoku (See FIG. 1). Sudoku is a straightforward form of a CSP (22). The designed architecture corresponds to a graph neural network; node attributes (in Sudoku, integers from 1-9) are embedded in a 128-dimensional space and later subjected to edge convolution taking into account edge indices (See FIG. 5). 30 million solved Sudoku grids were generated, and marking approximately half of the numbers in each grid as missing, the network was trained to reconstruct those numbers by minimizing the cross-entropy loss between network predictions and the actual values. The final graph neural network performs quite well on solving Sudoku puzzles (See FIG. 5); and this network architecture, having been validated for Sudoku puzzles, was then applied on protein sequences.

Given the optimal architecture for CSPs from Sudoku, the neural network having this architecture was trained on sequences from UniParc; using their mapping to PDB structures, the corresponding distance matrices were automatically extracted. It was observed that training accuracy saturates at around 2 million sequences (out of 70 million total mapped to Gene3D). Reconstruction accuracy is considerably lower than Sudoku (See FIG. 7), as was expected: the Sudoku CSP has a single well-defined solution, thus an accuracy approaching 1 is possible. By contrast, each protein adjacency matrix can be adopted by many different sequences. The achieved accuracy of around 40% roughly corresponds to the common level of sequence identity within a protein fold (16). Evaluating the trained experimental network by having it reconstruct given sequences (See FIG. 7F), it was noted that even when removing the majority of the residues, a majority of sequences is reconstructed with an expected sequence identity of about 40%.

It was then examined whether network scores for single mutations can be predictive of whether that mutation is stabilizing or destabilizing; presumably, a destabilizing mutation would also disrupt some of the constraints in the CSP and would thus be scored unfavourably by the graph neural network. It was observed that a relatively strong correlation is achieved (Pearson R: 0.42) with experimentally measured mutations from Protherm (23) (See FIG. S1). Classical and statistical methods such as Rosetta, FoldX or Elaspic have long been in use for this problem and perform quite well, and indeed somewhat better than the designed experimental network (24-26) (Rosetta obtaining Pearson R: 0.56 in our hands, see FIG. S1). However, it should be noted that the designed experimental network was not optimized for this particular task (and was never trained on any ΔΔG data); indeed, since many or even most mutations in the data set would still allow the sequence satisfy the CSP (and the protein to fold). Hence, the designed experimental network may not even be expected to perform well at this particular task. It was also observed that evaluation using the designed experimental network is vastly faster than classical methods (see below).

As the designed experimental graph network is able to reconstruct sequences with missing residues and score mutations with relatively high accuracy, the designed experimental network was applied to generate entire sequences for a given structure (adjacency matrix). This corresponds to de novo protein design—designing a novel sequence for a given fold. To this end, four protein folds that had been left out of the training set are used and cover the breadth of the CATH hierarchy. An A*-like algorithm was used to obtain sequences that score highly with the designed experimental network. In conventional protein design both A* and dead-end elimination, as well as Markov-chain monte carlo sampling approaches to obtain sequences scored by a classical forcefield have been applied (27, 28). However, this has remained a difficult problem, in part due to the great computational cost involved. Due to many factors, including the fact that the designed experimental network does not require rotamer optimization to properly evaluate a single sequence, evaluation using the designed experimental network is many orders of magnitude faster than current protein design methods (See Table S1).

The top 20,000 (10%) generated sequences as scored by the designed experimental network for each of the 4 folds were chosen for further evaluation. First, QUARK (30) was used, a de novo (not template-based) structure prediction algorithm to obtain structures for the generated sequences; for all four folds the obtained structures match the initial PDB structure (that corresponds to the distance matrix used to generate the sequences) almost exactly (See FIGS. 8A-D). The quality of the reconstruction was evaluated using a number of computational metrics, including Modeller molpdf and Rosetta REU. In all cases, the scores are in the same range or better than the target structure, suggesting that the sequences that the designed experimental network generated do novo indeed fold in the shape corresponding to the adjacency matrix (See FIGS. 3E, 8F). For a final computational evaluation, 100 ns molecular dynamics was run on each structure, including the target structures. It was observed that in most cases, the target structure and the structures predicted for the designed sequences show similar root mean square fluctuation in the MD simulation, again suggesting that the generated sequences fold into the predetermined structure (See FIGS. 9A-D).

Finally, two generated sequences and their corresponding sequences of the target structures were chosen (for the albumin and racemase structural templates) to evaluate experimentally. Each sequence was ordered and expressed them as his-tagged constructs for Ni-NTA affinity purification. After purification, the secondary structure of each protein was evaluated using circular dichroism spectroscopy (CD). Each secondary structure element has a distinctive absorbance spectrum in the far-UV region, thus similar folds should present similar absorbance spectra. It was observed that both sequences show a CD spectrum very similar to the native sequences. Taken together with the rest of the evidence from molecular dynamics, Modeller and Rosetta assessment scores, this strongly suggests that these generated sequences adopt the predetermined fold (see FIGS. 9E and 9F). This is particularly striking in the case of the albumin template where the spectra are indistinguishable (FIG. 9E). The designed sequence from the racemase template displayed a considerable loss of solubility compared to

TABLE S1

| Name | Website |
| --- | --- |
| uniparc_xml_parser | https://gitlab.com/kimlab/uniparc_xml_parser |
| uniparc_all.xml.gz | http://www.uniprot.org/downloads |
| uniparc | https://gitlab.com/datapkg/uniparc |
| uniparc-domain | https://gitlab.com/datapkg/uniparc-domain |
| kmbio | https://gitlab.com/kimlab/kmbio |
| PDB | ftp://ftp.wwpdb.org/pub/pdb/data/structures/divided/ |
| pdb-analysis | https://gitlab.com/datapkg/pdb-analysis |
| uniparc-domain-wstructure | https://gitlab.com/datapkg/uniparc-domain-wstructure |
| proteinsolver | https://gitlab.com/kimlab/proteinsolver |

For the four folds (mainly α, serum albumin; mainly β, PDZ3 domain; mainly β immunoglobulin; α+β, alanine racemase), 200,000 sequences each using A* search were generated using the designed experimental network. It was observed that the sequences tend to fall within 37-44% sequence identity with the native sequence, in line with the sequence identity within the respective protein families (See FIGS. S2-S5). As no information about the sequences was provided to the algorithm, this suggests that it was able to learn significant features of protein structure. It was also observed that when predicting secondary structure of the sequences (29), it matches the target secondary structures almost exactly (See FIGS. S2-S5).

the sequence from the target structure. Although this made its characterization challenging, a clear spectrum was obtained by combining a low ionic strength buffer (10 mM Na-phosphate, pH 8) with a 10 mm cuvette. While the resulting CD spectrum is somewhat different from the target, this may be due to technical issues resulting from low solubility or a more dynamic nature of the designed protein (consistent with the molecular dynamics in FIG. 9C); the spectrum definitely corresponds to a folded helical structure consistent with the predetermined fold.

It was observed that the designed experimental graph neural network approach to protein design showed remarkable accuracy in generating novel protein sequences that fold into a predetermined fold. Previous approaches were hampered by the enormous computational complexity, in particular when taking into account backbone flexibility. The described graph network approach sidesteps this problem and delivers accurate designs for a wide range of folds. It is expected that the design neural network would be able to generate sequence for completely novel imagined protein folds. As a neural network approach, its evaluation is many orders of magnitude faster than classical approaches that will enable the exploration of vastly more potential backbones.

Detailed Description of the Experimental Neural Network

Data Preparation

The websites which host the code and data that were used to generate those datasets are listed in Table S1. In brief, it was downloaded from UniParc (1) a dataset of all protein sequences and corresponding domain definitions, and it was extracted from this dataset a list of all unique Gene3D domains. The PDB database was also processed to extract the amino acid sequence and the distance matrix of every chain in every structure. For each amino acid, the distances of all other residues below a cut-off of 12 Angstrom was recorded in the distance matrix (edge attribute dataset), taking into account the closest heavy atom (including the side chain). Finally, an attempt was made to find a structural template for every Gene3D domain sequence, and the resulting adjacency matrix from the structural template is associated to that sequence.

The end result of this process is a dataset of 72,464,122 sequences and adjacency matrices, clustered into 1,373 different Gene3D superfamilies. This initial dataset was split into a training subset, containing sequences of 1,029 Gene3D superfamilies, a validation subset, containing sequences of 172 Gene3D superfamilies, and a test subset, containing sequences of another 172 Gene3D superfamilies.

Network Architecture

The Sudoku problem was initially used to optimize the network architecture, including the dimensionality of the embedding space (ex: 128) the number of residual blocks (ex: 4), the edge embedding (ex: 2-layer feed-forward network with 256 elements in the hidden layer), the use of batch normalization as well as the choice of non-linearity (ReLU). The architecture of the ProteinSolver graph neural network is presented in FIG. 5. The network takes as input a set of node attributes, a set of edge indices, and optionally, a set of edge attributes. The node and edge attributes are embedded into a 128-dimensional space, followed by the application of batch normalization (BatchNorm) (2) and a rectified linear unit (ReLU) (3) nonlinearity.

The node and edge attributes, and the edge indices, are then passed into a graph convolution residual block, which produces a new set of node and edge attributes with the same dimensionality as the inputs but endowed with information about the immediate neighborhood of each node. The produced node and edge attributes are added to the inputs, and the resulting tensors are passed through a ReLU layer and into the subsequent graph convolution residual block, with four residual blocks being applied in total. The node attributes produced by the last residual block are passed through a rectified linear unit nonlinearity and into a final Linear layer, which maps the 128 features describing each node into an N-dimensional space, where N is the number of possible output values (i.e. 9 in the case of Sudoku; 20 in the case of protein design). The outputs from the Linear layer can optionally be passed through a softmax activation function in order to convert the raw output values into probabilities of a given node possessing a given label.

The primary component of the graph convolution residual block is the Edge Convolution (EdgeConv) layer (4), which for every edge in the graph, concatenates the edge attributes and the attributes of the interacting nodes and passes the resulting vector through a multi-layer perceptron (see FIG. 5). The outputs of the multilayer perceptron form the new edge attributes, and summing over the edge attributes of each of the nodes produces the new node attributes. The node and edge attributes are normalized using a BatchNorm layer and are added to the input tensors, which completes the residual block.

Network Training

The architecture and the hyperparameters of the Protein-Solver network were optimized by training the network to solve Sudoku puzzles, which is a well-defined problem and for which predictions made by the network can easily be verified. Sudoku puzzles are treated as graphs having 81 nodes, corresponding to squares on the Sudoku grid, and 1701 edges, corresponding to pairs of nodes that cannot be assigned the same number (see FIG. 1). The node attributes correspond to the numbers entered into the squares, with an additional attribute to indicate that no number has been entered, the edge indices correspond to the 1701 pairs of nodes that are constrained such that they cannot have the same number, and the edge attributes are empty because all edges in the graph impose identical constraints.

30 million solved Sudoku grids are generated, and marking approximately half of the numbers in each grid as missing, the network was trained to reconstruct those numbers by minimizing the cross-entropy loss between predicted and actual values. Throughout training, the accuracy that the network achieves on the training dataset was tracked (FIG. 7A, blue line) and on the validation dataset (FIG. 7A, orange line), which contains computer-generated Sudoku puzzles that have a unique solution, and the training was stopped once the validation accuracy had reached a plateau. The accuracy that is achieved on the validation dataset is much higher than the accuracy achieved on the training dataset because the unsolved Sudoku grids given during training do not necessarily have a unique solution. After trying multiple different network architectures and different hyperparameters, it was observed that the highest validation accuracy is achieved using a graph neural network with four or more graph convolution residual blocks, 128-dimensional node and edge attribute embeddings, EdgeConv layers containing a two-layer feedforward network with 256 neurons in the hidden layer, ReLU nonlinearities, and batch normalization that is applied before, rather than after, the outputs of the residual blocks are added to the input channels. The test accuracy of the trained network was evaluated using a dataset comprised of 30 curated Sudoku puzzles collected from http://1sudoku.com (5, 6) (FIG. 2B,C).

After optimizing the network architecture for solving Sudoku puzzles, the same designed experimental network was applied to protein sequence generation, which is a less well-defined problem than Sudoku and for which the accuracy of predictions is more difficult to ascertain. In treating proteins as graphs, where nodes correspond to the individual amino acids and edges correspond to shortest distances between pairs of amino acids, considering only those pairs of amino acids that are within 12 Å of one another. The node attributes specify the amino acid type, with an additional flag to indicate that the amino acid type is not known, while the edge attributes include the shortest distance between each pair of amino acids in Cartesian space and the number of residues separating the pair of amino acids along the protein chain. For each domain sequence in the training dataset, approximately half of the amino acids in the sequence were marked as missing, and the network was trained to reconstruct the masked amino acids by minimizing the cross-entropy loss between predicted and actual values (FIG. 7D). The edge attributes corresponding to each training example were passed into the network without modification. Throughout training, the accuracy with which the network can reconstruct amino acid sequences from there training and validation datasets were tracked where, in both cases, half of the amino acids were marked as missing (FIG. 7D), and training was terminated once the validation accuracy appeared to have reached a plateau. The trained network was evaluated by examining how well it can reconstruct sequences from the test dataset using edge attributes alone and without any sequence information (FIG. 7E), by measuring the correlation between differences in network outputs for wild type and mutant residues and the change in the Gibbs free energy of folding ($\Delta\Delta G$) associated with mutations (7) (Supp. FIG. S1A). In the case of sequence reconstruction, a bimodal distribution was observed in sequence identities between generated and reference sequences, with a smaller peak around 7% sequence identity, corresponding to generated sequences that share little or no homology with the reference sequences, and a larger peak around 40% sequence identity, corresponding to generated sequences that share substantial homology with the reference sequences (FIG. 2E). While the fraction of designs falling into the second category increases when the network is provided with some of the original residues (FIG. 7F), there are still some cases where the generated and the reference sequences share little homology despite 80% of the original residues being given as input (FIG. 7F).

In the case of $\Delta\Delta G$ prediction, it was observed that the network can predict the $\Delta\Delta G$ associated with mutations with a Spearman's correlation coefficient of 0.426, despite never having been trained specifically for this task (Supp. FIG. 1A).

Solving Puzzles and Generation of Novel Sequences

Two different strategies to generate or complete CSPs were used: one-shot generation and incremental generation. In one-shot generation, the input partially filled sequence with the missing labels was passed through the network only once, for every node accepting the label assigned the highest probability by the network. In incremental generation, the input partially filed sequence was passed through the network once for every missing label. At each iteration, the label for which the network has the most confident prediction is selected, and that label is treated as being known in the subsequent iteration.

In order to generate a library of highly probable solutions, a strategy similar to A* search (9) was used, which allows for achieving a compromise between the accuracy provided by exhaustive breadth-first search and the speed provided by greedy search. As with the incremental generation strategy described above, each time the input is passed through the network, at least a single one node for which the network is making the most confident predictions is selected. However, instead of accepting for that node the label with the highest probability, all labels that have a probability above a threshold of 0.05 are accepted, and the inputs partially filled with the accepted labels is added to a priority queue. Next, from the priority queue, a partially filled input with the highest priority is extracted, extend it by one iteration, and place the results back onto the priority queue. This process is repeated until the desired number of solutions are generated.

The priority Pj, which is assigned to every partially filled input placed on the priority queue, is defined by Equation 1. Here, $p_i$ is the probability assigned by the network to the label accepted at iteration i, and p* is the expected maximum probability that the network will assign to labels that are accepted in the subsequent iterations. p* is a tunable parameter which controls how much the algorithm resembles greedy search vs. exhaustive breadth-first search. If p* is set to 0, the algorithm is equivalent to the incremental generation algorithm described above, where the most probable output from the previous iteration is immediately accepted. On the other hand, if p* is set to 1, the algorithm is equivalent to exhaustive breadth-first search, where the network is used to extend every possible label at a given iteration before moving on to the next iteration.

$$P_j = \sum_{i=1}^{j} \log(p_i) + \sum_{j}^{N} \log(p^*)$$

On a single Titan Xp GPU, generation of 100,000 sequences for an average protein domain takes about 30 minutes.

Molecular Dynamics

All water and ions atoms were removed from the structure with PDB codes 1 N5U, 4Z8J, 4UNU, and 1OC7, corresponding to an all-$\alpha$ protein, a mainly-$\beta$ protein, an all-$\beta$ protein and a mix-$\alpha\beta$ protein, respectively. The structural models for the generated sequences were produced using Modeller, with the PDB files described above serving as templates. Using TLEAP in AMBER16 (10) and AMBER ff14SB force field (11), the structures were solvated by adding a 12 nm3 box of explicit water molecules, TIP3P. Next, Na+ and Cl– counter-ions were added to neutralize the overall system net charge, and periodic boundary conditions were applied. Following this, the structures were minimized, equilibrated, heated over 800 ps to 300 K, and the positional restraints were gradually removed. Bonds to hydrogen were constrained using SHAKE (12) and a 2 fs time step was used. The particle mesh Ewald (13) algorithm was used to treat long-range interactions.

Experimental Validation

Protein Purification.

All constructs were synthetized by Invitrogen GeneArt Synthesis (ThermoFisher) as Gene Strings. The constructs design included flanking BamHI and HindIII restriction sites for subcloning into a N-terminal 6×His-tagged pRSet A vector. All genes were codon optimized for expression in *E. coli* using the GeneArt suite.

The pRSET A constructs were transformed into chemically competent *E. coli* OverExpress C41(DE3) cells (Lucigen) by heat shock and plated on LB-Carbenicillin plates. Colonies were grown in 15 ml of 2×YT media containing Carbenicillin (50 μg/mL) at 37° C., 220 rpm until the optical density (O.D.) at 600 nm reached 0.6. Cultures were then induced with IPTG (0.5 mM) for 3 h at 37° C. Cells were pelleted by centrifugation at 3000 g (4° C., 10 min) and resuspended in 1 ml of BugBuster Master Mix (Millipore). The lysate mixtures were incubated for 20 min in a rotating shaker and the insoluble fraction was removed by centrifugation at 16000 g for 1 min. For a 15 ml preparation, 200 μl of Ni-NTA Agarose (QIAGEN) were pre-washed in Phosphate-buffered saline (PBS) and added to the supernatant from the cell lysate for 20 min at 4° C. in batch. The bound beads were washed thrice with PBS (1 mL) containing 30 mM of imidazole to prevent nonspecific interaction of lysate proteins. Proteins were eluted using PBS buffer with 500 mM imidazole and dialyzed against PBS (14).

Protein concentration was calculated using the Pierce BCA Protein Assay Kit (ThermoFisher). The concentration of 4beu_Design was corroborated by absorbance at 205 nm as described by Anthis et. al. (15). 1n5u and 1n5u_Design and 4beu eluted solubly at concentrations around 200-400 ug/ml. 4beu_Design presented a limit of solubility at around 15 ug/ml. Sample purity was assessed through Coomassie staining on SDS-PAGE with 4-20% Mini-PROTEAN TGX Precast Protein Gels, 10-well (Bio-Rad) and Mass Spectrometry (ESI).

Circular Dichroism

All CD measurements were made on a Jasco J-810 CD spectrometer in 1 mm Quartz Glass cuvette for high performance (QS) (Hellma Analytics) with the exception of 4beu_Design where a 10 mm Quartz Glass cuvette (QS) (Hellma Analytics) was preferred. 1 n5u and 1n5u_Design were analysed in PBS whereas 4beu and 4beu_Dopa were analysed in 10 mM Na-Phosphate, pH 8. The CD spectrum was measured between 198 nm and 260 nm wavelengths using a 1 nm of bandwidth and 1 nm intervals collected at 50 nm/min; each reading was repeated ten times. All measurements were taken at 20° C.

Code Availability

The source code for ProteinSolver will be freely available at https://gitlab.com/ostrokach/proteinsolver.

The network was implemented in the Python programming language using PyTorch (16) and PyTorch Geometric (17) libraries. The repository also includes Jupyter notebooks that can be used to reproduce all the figures presented in this manuscript.

Figures Caption

FIG. 5. Deep graph neural network to solve the protein design problem. The problem is phrased as a constraint satisfaction problem with different amino acids putting constraints on other amino acids that are spatially close. These constraints can be represented as a distance matrix and are analogous to the constraints given to different numbers in the puzzle Sudoku (where a constraint matrix is also given). This allowed for devising and optimizing the solver graph neural network architecture. This architecture embeds both edge and node attributes in an X-dimensional space, and given the edge indices (i.e., the graph), they are subjected to a two layer edge convolution. This architecture then efficiently solves Sudoku puzzles and generates accurate protein sequences.

Figure 7:
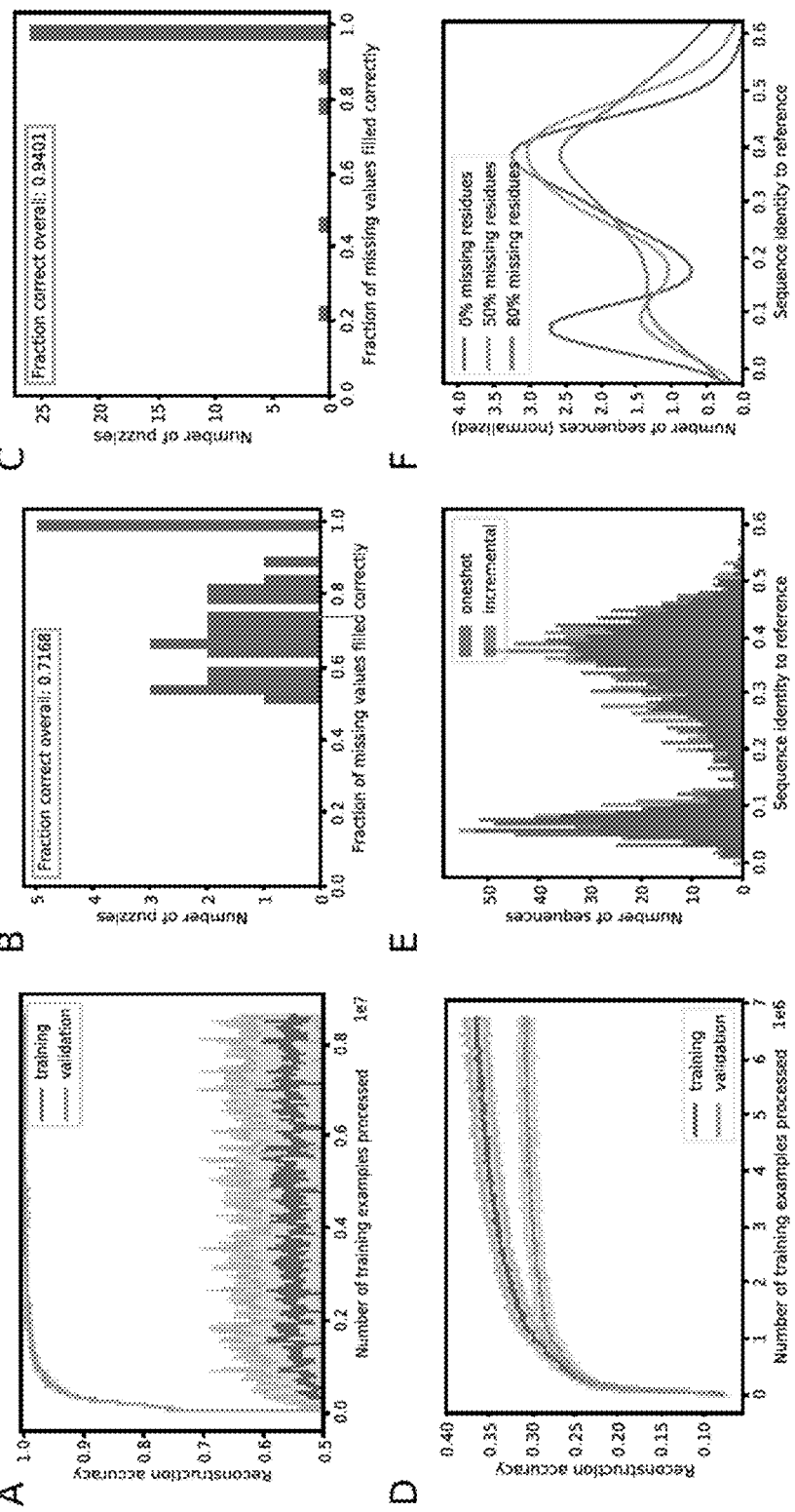
FIG. 7 illustrates performance of generated experimental neural network systems applied to a Sudoku CSP and the problem of generating protein sequences.

FIG. 7. (A) Training and validation accuracy of a solver graph neural network according to an example embodiment trained to solve sudoku. The training dataset is comprised of 30 million solved sudoku grids. The inputs to the network were constructed by removing 50% of the values from each sudoku grid. The validation dataset is comprised of 200 computer-generated sudoku puzzles and solutions. The difficulty of validation puzzles is much lower than the difficulty of sudoku puzzles that are typically played by humans. (B, C) Accuracy achieved by a trained solver network on the test dataset, comprised of 30 sudoku puzzles scraped from 1sudoku.com. In the case of (B), predictions were made using a single pass through the network. In the case of (C), predictions were made by running the network repeatedly, each time taking a single prediction in which the network is the most confident. (D) Training and validation accuracy of a solver graph neural network according to an example embodiment trained to predict missing amino acids. The network was trained using 1 million protein sequences and adjacency matrices, with 50% of the sequence marked as missing. The validation dataset is comprised of 200 sequences and adjacency matrices of proteins with a different shape (Gene3d domain) than proteins in the training dataset. (E) Accuracy achieved by a trained solver network on the test dataset, comprised of 10,000 sequences and adjacency matrices of proteins with a different shape (Gene3d domain) than proteins in the training and validation datasets. In the case of blue bars, predictions were made using a single pass through the network. In the case of red bars, predictions were made by running the network repeatedly, each time taking a single prediction in which the network is the most confident. (F) The identity of generated sequences to the reference sequence, depending on the fraction of amino acids that are made available to the model.

Figure 8:
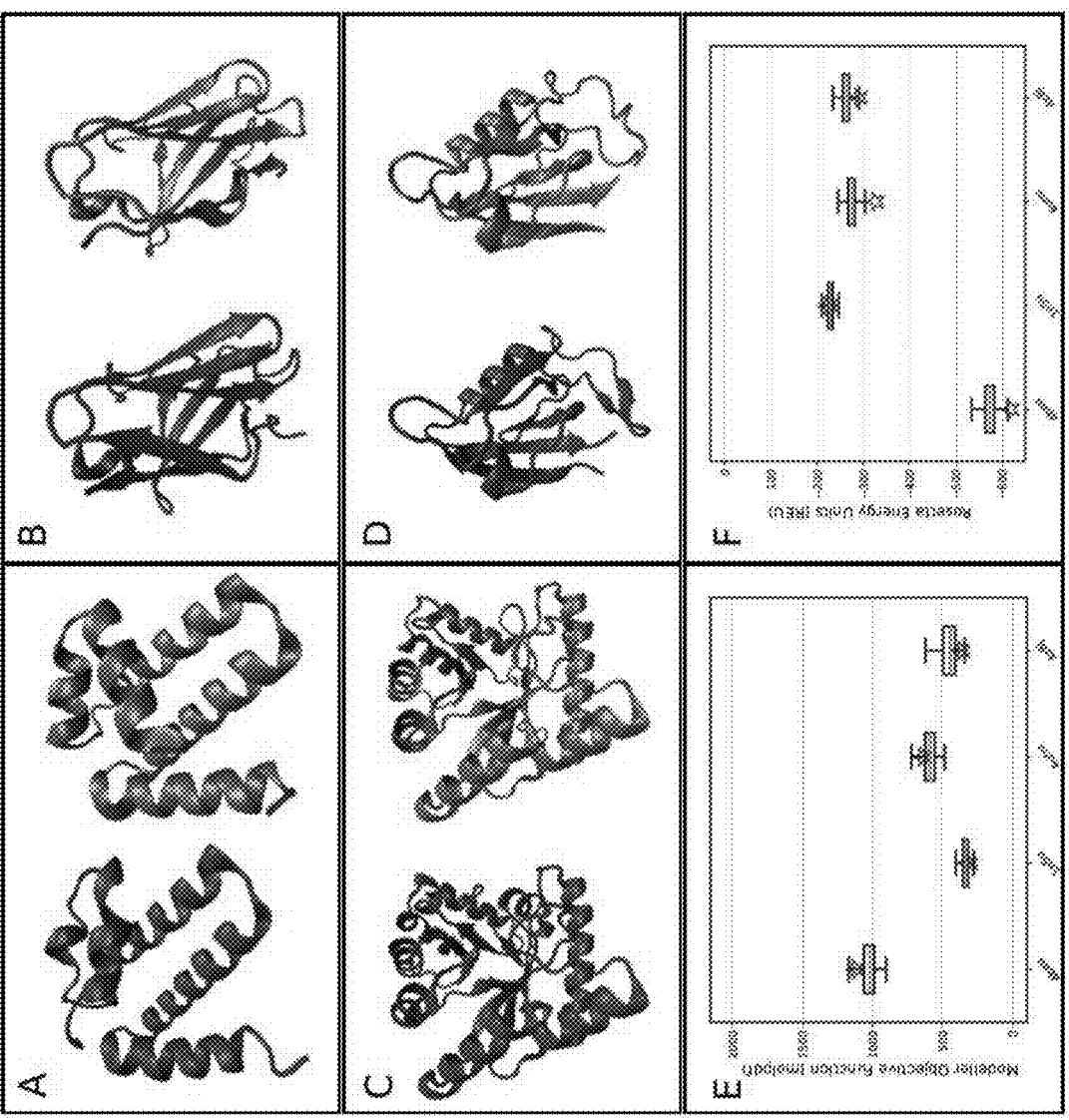
FIG. 8 illustrates generated sequences that fold into the four main folding classes ($\alpha$, $\beta+\alpha$, $\beta/\alpha$ and $\beta$) and the scores computed by Modeller (molPDF, lower is better) and Rosetta (Rosetta Energy Units, lower is better) for 20,000 structures constructed for the experimental neural network-designed sequences.

FIG. 8. Generating sequences that fold into the four main folding classes ($\alpha$, $\beta+\alpha$, $\beta/\alpha$ and $\beta$). (A) serum albumin (pdb_id: 1n5u), which is mostly comprised of alpha helices. (B) immunoglobulin (pdb_id: 4unu), a protein containing mainly beta sheets. (C) alanine racemase (pdb_id: 4beu), a protein containing both alpha helices and beta sheets. (D) PDZ3 domain (pdb_id:4z8j), which is mostly comprised of beta sheets. For each protein, the target structure (from which the adjacency matrix was extracted) is shown on the left, and the structure of the ProteinSolver-designed sequence (based on this adjacency matrix) is shown on the right. The structure of the ProteinSolver-designed sequence was generated by QUARK using, as input, the sequence with the highest network score. The rms between the structures (i.e., target vs QUARK) are 3.35 A, 1.5 A, 1.05 A and 1.64 A for (A), (B), (C) and (D), respectively. Finally, (E) and (F) show the scores computed by Modeller (molPDF, lower is better) and Rosetta (Rosetta Energy Units, lower is better), respectively, for 20,000 structures constructed for ProteinSolver-designed sequences. The measures calculated for the target structures are shown as stars in the plots.

Figure 9:
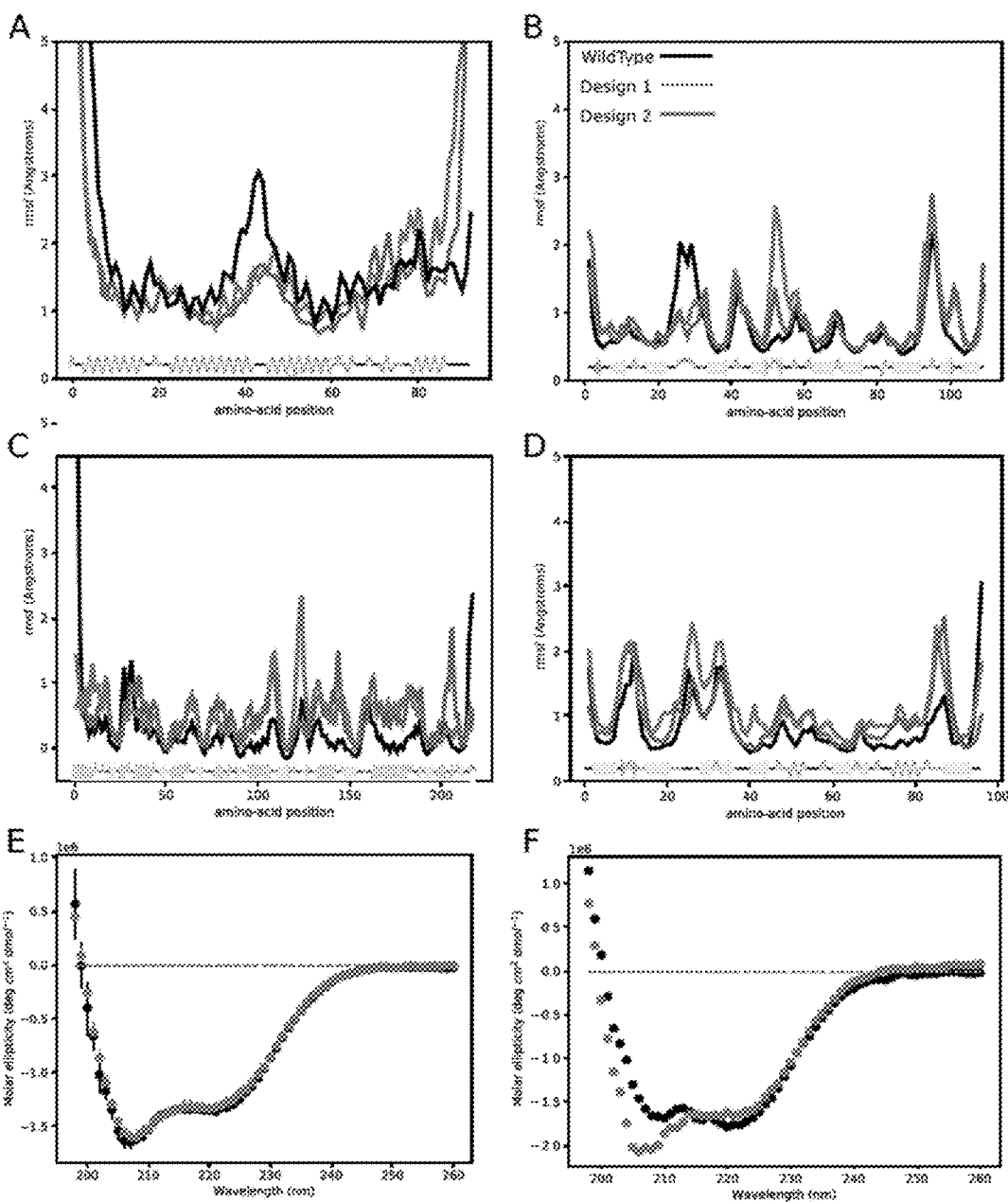
FIG. 9. Illustrates molecular dynamics simulations of the target protein structures and the de novo designs using the experimental neural network-designed sequences to validate stability of the designed structures.

FIG. 9. Molecular Dynamics and CD experiments. To validate that the generated sequences indeed adopt the pre-determined structures, computational and experimental methods were used. Computationally, 100 ns molecular dynamics simulations with both the protein in the target structure and the designed neural network were performed (A-D). In all four cases, the generated sequences show comparable fluctuation in molecular dynamics to the original target proteins, indicating that they are of comparable stability as the target and thus stably folded. (E,F) Two of the generated sequences were experimentally expressed and their structure were tested using circular dichroism spectroscopy. It was observed that they are definitely folded proteins in solutions and that they adopt the same (E) or very similar (F) structure as the protein that supplied the target structure.

Figure 10:
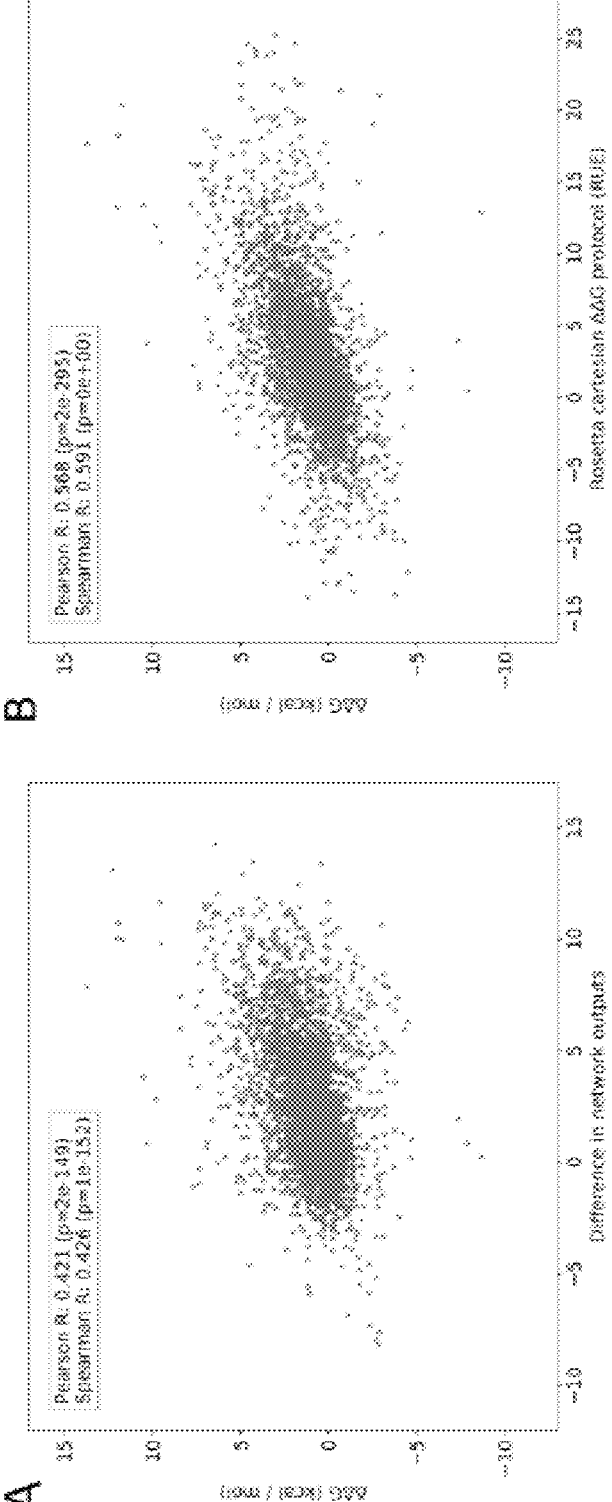
FIG. 10 illustrates performance graphs of correlations between in the Gibbs free energy of folding associated with mutations for predicted sequences from the experimental neural network and for predicted sequences made by Rosetta's Cartesian protocol.

FIG. 10. Correlations between changes in the Gibbs free energy of folding associated with mutations ($\Delta\Delta G$) for Protherm Dataset [7]. (A) Predictions made by the ProteinSolver network. (B) Predictions made by Rosetta's Cartesian protocols and the betanov15 energy functions, details are provided for reference in Table S3.

Figure 11:
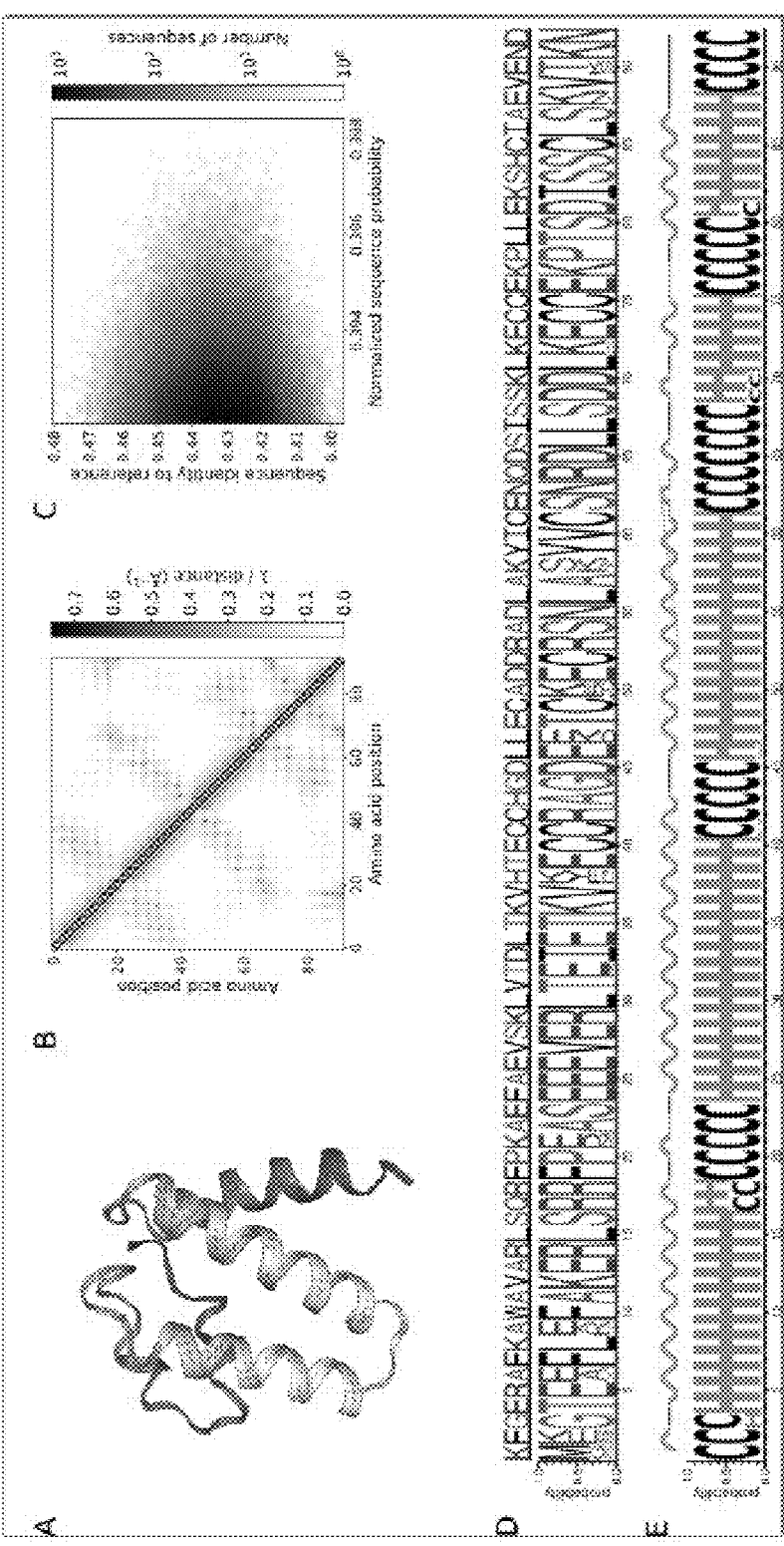
FIG. 11 illustrates the generated sequences that fold into a protein resembling the structure of serum albumin, which is mostly comprised of alpha helices.

FIG. 11. Generating sequences that fold into a protein resembling the structure of serum albumin, which is mostly comprised of alpha helices. (A) A representative structure of the serum albumin domain extracted from chain A of the PDB structure 1 n5u. (B) Amino acid contact map corresponding to the representative structure. (C) A diagram showing the probability assigned by the network to each of the 200,000 generated sequences, normalized by the length of the sequence, versus the sequence identity between the generated sequences and the reference sequence. (D)

Sequence LOGO of the 200,000 generated sequences. The amino acid sequence of the reference structure is displayed above the LOGO. (E) Secondary Structure Prediction performed by Psipred on 20.000 generated sequences. The secondary structure of the reference structure is displayed above the LOGO.

Figure 12:
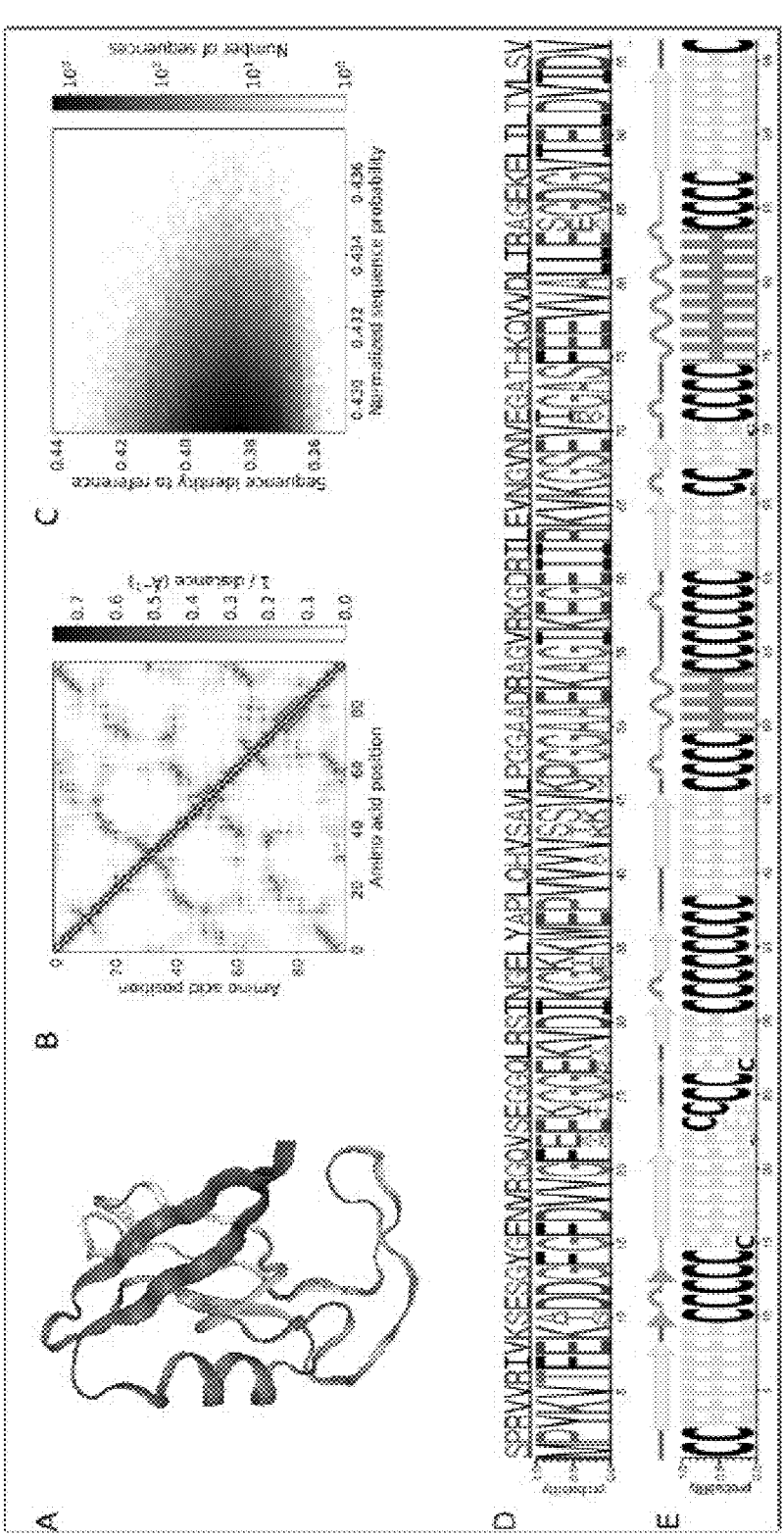
FIG. 12. illustrates generated sequences that fold into a protein resembling the structure of PDZ3 domain, which is mostly comprised of beta sheets.

FIG. 12. Generating sequences that fold into a protein resembling the structure of PDZ3 domain, which is mostly comprised of beta sheets. (A) A representative structure of the PDZ3 domain, extracted from chain A of the PDB structure 4z8j. (B) Amino acid contact map corresponding to the representative structure. (C) A diagram showing the probability assigned by the network to each of the 200,000 generated sequences, normalized by the length of the sequence, versus the sequence identity between the generated sequences and the reference sequence. (D) Sequence LOGO of the 200,000 generated sequences. The amino acid sequence of the reference structure is displayed above the LOGO. (E) Secondary Structure Prediction performed by Psipred on 20.000 generated sequences. The secondary structure of the reference structure is displayed above the LOGO.

Figure 13:
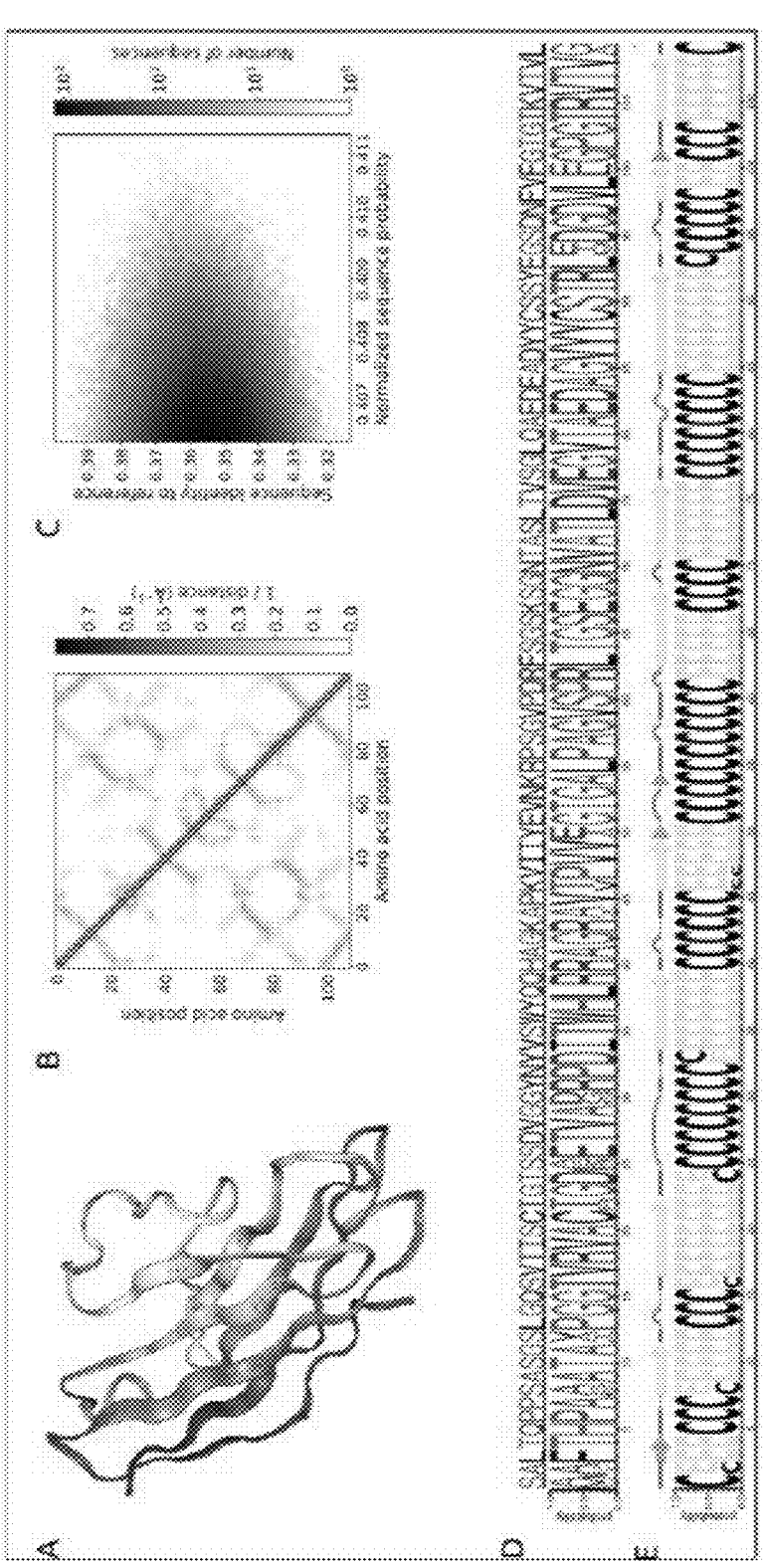
FIG. 13. illustrates generated sequences that fold into a protein resembling the structure of immunoglobulin, a protein containing mainly beta sheets.

FIG. 13. Generating sequences that fold into a protein resembling the structure of immunoglobulin, a protein containing mainly beta sheets. (A) A representative structure of the immunoglobulin domain extracted from chain A of the PDB structure 4unu. (B) Amino acid contact map corresponding to the representative structure. (C) A diagram showing the probability assigned by the network to each of the 200,000 generated sequences, normalized by the length of the sequence, versus the sequence identity between the generated sequences and the reference sequence. (D) Sequence LOGO of the 200,000 generated sequences. The amino acid sequence of the reference structure is displayed above the LOGO. (E) Secondary Structure Prediction performed by Psipred on 20.000 generated sequences. The secondary structure of the reference structure is displayed above the LOGO.

Figure 14:
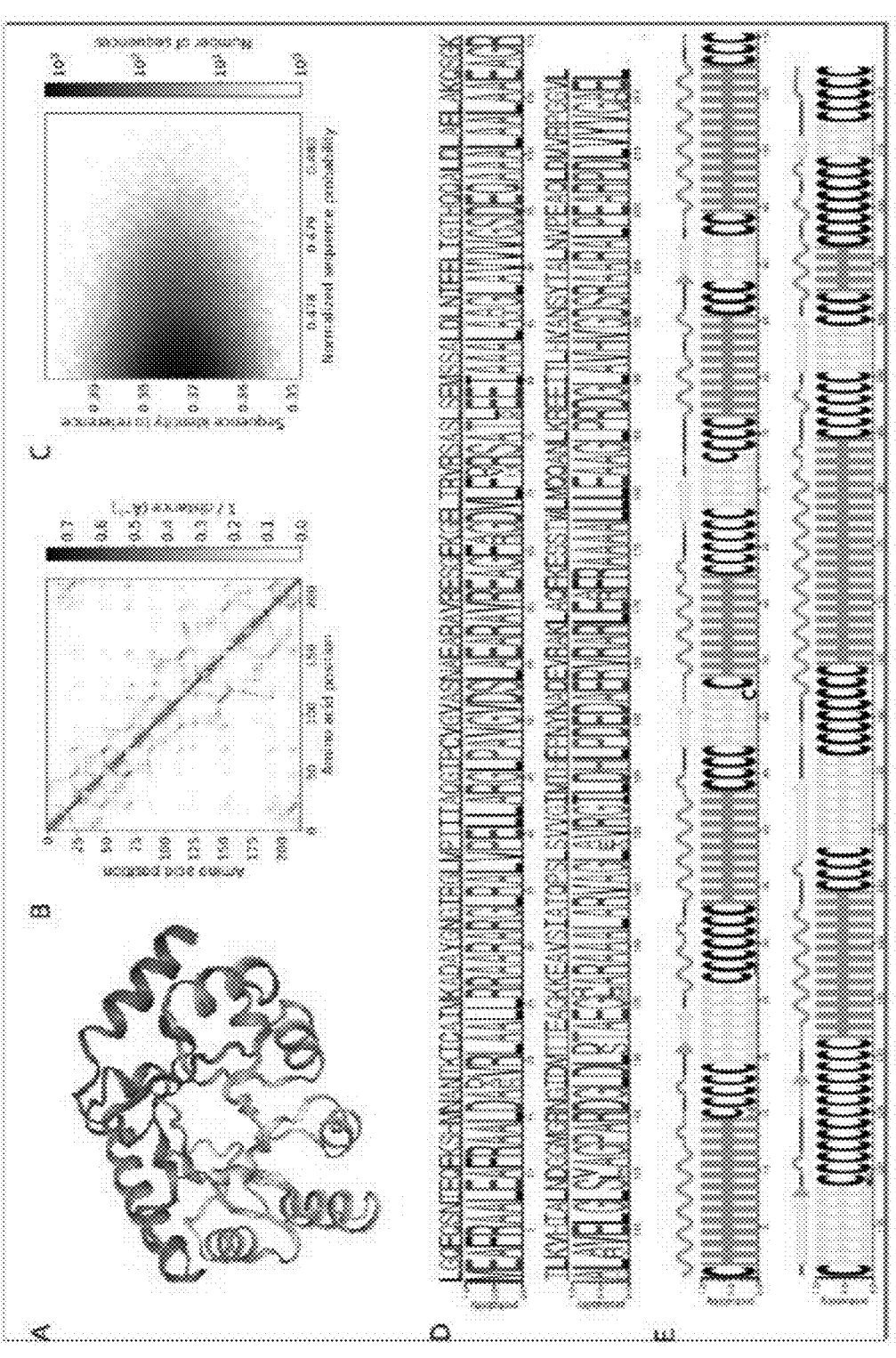
FIG. 14. illustrates generated sequences that fold into a protein resembling the structure of immunoglobulin, a protein containing mainly beta sheets.

FIG. 14. Generating sequences that fold into a protein resembling the structure of alanine racemase, a protein containing both alpha helices and beta sheets. (A) A representative structure of the alanine racemase domain extracted from chain A of the PDB structure 4beu. (B) Amino acid contact map corresponding to the representative structure. (C) A diagram showing the probability assigned by the network to each of the 200,000 generated sequences, normalized by the length of the sequence, versus the sequence identity between the generated sequences and the reference sequence. (D) Sequence LOGO of the 200,000 generated sequences. The amino acid sequence of the reference structure is displayed above the LOGO. (E) Secondary Structure Prediction performed by Psipred on 20.000 generated sequences. The secondary structure of the reference structure is displayed above the LOGO.

Figure 15:
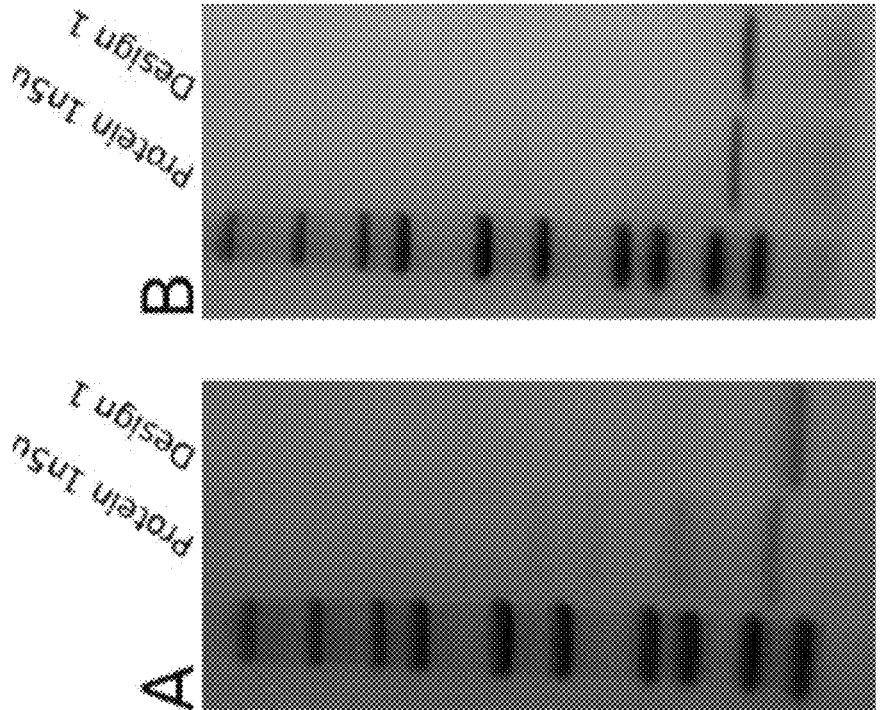
FIG. 15. illustrates the designed albumin sequence and its natural counterpart (pdb-id: 1n5u) analyzed by SDS-PAGE in (A) oxidizing and (B) reducing conditions (1 mM DTT).

FIG. 15. The designed albumin sequence and its natural counterpart (pdb-id: 1n5u) were analyzed by SDS-PAGE in (A) oxidizing and (B) reducing conditions (1 mM DTT). The natural protein, with an unpaired cysteine, forms high MW species not present in reducing conditions. The Design 1 is only represented as a single band in both environments. Interestingly, the chosen sequence from the albumin template contains 4 pairs of potential disulfide bonds, whereas it is known that the albumin template used has only 3 of these bonds (PDB 1 n5u). The designed 1 n5u run in an SDS-PAGE in oxidising conditions as a single band. Furthermore, the mass spectrometry analysis by electrospray (ESI) of the molecular weight (MW) of designed 1 n5u showed a loss of 8 Da against the theoretical MW, consistent with the loss of 8 protons. All together this indicates that a new disulfide bond not present in the albumin structural template was efficiently inserted into the designed sequence.

REFERENCES

1. M. C. Deller, L. Kong, B. Rupp, Protein stability: a crystallographer's perspective. *Acta Crystallogr. Sect. F Struct. Biol. Commun.* 72, 72-95 (2016).
2. A. S. Bommarius, M. F. Paye, Stabilizing biocatalysts. *Chem. Soc. Rev.* 42, 6534-6565 (2013).
3. S. Fischman, Y. Ofran, Computational design of antibodies. *Curr. Opin. Struct. Biol.* 51, 156-162 (2018).
4. A. Chevalier et al., Massively parallel de novo protein design for targeted therapeutics. *Nature.* 550, 74-79 (2017).
5. D. Shultis et al., Changing the Apoptosis Pathway through Evolutionary Protein Design. *J. Mol. Biol.* 431, 825-841 (2019).
6. M. G. F. Sun, P. M. Kim, Data driven flexible backbone protein design. *PLOS* Comput. Biol. 13, e1005722 (2017).
7. S. Khan, M. Vihinen, Performance of protein stability predictors. *Hum. Mutat.* 31, 675-684 (2010).
8. B. M. Kroncke et al., Documentation of an Imperative To Improve Methods for Predicting Membrane Protein Stability. *Biochemistry.* 55, 5002-5009 (2016).
9. M. G. F. Sun, M.-H. Seo, S. Nim, C. Corbi-Verge, P. M. Kim, Protein engineering by highly parallel screening of computationally designed variants. *Sci. Adv.* 2, e1600692 (2016).
10. G. J. Rocklin et al., Global analysis of protein folding using massively parallel design, synthesis, and testing. *Science.* 357, 168-175 (2017).
11. A. D. Ullah, K. Steinhöfel, A hybrid approach to protein folding problem integrating constraint programming with local search. *BMC Bioinformatics.* 11 Suppl 1, S39-S39 (2010).
12. A. Dal Palù, A. Dovier, F. Fogolari, Constraint Logic Programming approach to protein structure prediction. *BMC Bioinformatics.* 5, 186 (2004).
13. J. Kocić, N. Jovičić, V. Drndarević, An End-to-End Deep Neural Network for Autonomous Driving Designed for Embedded Automotive Platforms. *Sensors.* 19 (2019), doi:10.3390/s19092064.
14. D. Silver et al., Mastering the game of Go without human knowledge. *Nature.* 550, 354 (2017).
15. M. Wainberg, D. Merico, A. Delong, B. J. Frey, Deep learning in biomedicine. *Nat. Biotechnol.* 36, 829 (2018).
16. N. L. Dawson et al., CATH: an expanded resource to predict protein function through structure and sequence. *Nucleic Acids Res.* 45, D289-D295 (2016).
17. J. Wang, H. Cao, J. Z. H. Zhang, Y. Qi, Computational Protein Design with Deep Learning Neural Networks. *Sci. Rep.* 8, 6349 (2018).
18. Z. Li, Y. Yang, E. Faraggi, J. Zhan, Y. Zhou, Direct prediction of profiles of sequences compatible with a protein structure by neural networks with fragment-based local and energy-based nonlocal profiles. *Proteins Struct. Funct. Bioinforma.* 82, 2565-2573 (2014).
19. T. E. Lewis et al., Gene3D: Extensive prediction of globular domains in proteins. *Nucleic Acids Res.* 46, D1282-D1282 (2017).
20. R. B. Palm, U. Paquet, O. Winther, Recurrent Relational Networks. *ArXiv*171108028 *Cs* (2017) (available at http://arxiv.org/abs/1711.08028).

21. M. O. R. Prates, P. H. C. Avelar, H. Lemos, L. Lamb, M. Vardi, Learning to Solve NP-Complete Problems—A Graph Neural Network for Decision TSP. *ArXiv*180902721 *Cs Stat* (2018) (available at http://arxiv.org/abs/1809.02721).

22. H. Simonis, in CP Workshop on modeling and reformulating Constraint Satisfaction Problems (2005), vol. 12, pp. 13-27.

23. K. A. Bava, M. M. Gromiha, H. Uedaira, K. Kitajima, A. Sarai, ProTherm, version 4.0: thermodynamic database for proteins and mutants. *Nucleic Acids Res.* 32, D120-D121 (2004).

24. H. Park et al., Simultaneous Optimization of Biomolecular Energy Functions on Features from Small Molecules and Macromolecules. *J. Chem. Theory Comput.* 12, 6201-6212 (2016).

25. J. Schymkowitz et al., The FoldX web server: an online force field. *Nucleic Acids Res.* 33, W382-W388 (2005).

26. D. K. Witvliet et al., ELASPIC web-server: proteome-wide structure-based prediction of mutation effects on protein stability and binding affinity. *Bioinforma. Oxf. Engl.* 32, 1589-1591 (2016).

27. J. Desmet, M. D. Maeyer, B. Hazes, I. Lasters, The dead-end elimination theorem and its use in protein side-chain positioning. *Nature.* 356, 539-542 (1992).

28. A. R. Leach, A. P. Lemon, Exploring the conformational space of protein side chains using dead-end elimination and the A* algorithm. *Proteins Struct. Funct. Bioinforma.* 33, 227-239 (1998).

29. L. J. McGuffin, K. Bryson, D. T. Jones, The PSIPRED protein structure prediction server. *Bioinformatics.* 16, 404-405 (2000).

30. D. Xu, Y. Zhang, Ab initio protein structure assembly using continuous structure fragments and optimized knowledge-based force field. *Proteins Struct. Funct. Bioinforma.* 80, 1715-1735 (2012).

The invention claimed is:

1. A method for generating a protein sequence, the method comprising:

receiving an empty or partially filled sequence of node elements, each node element of the sequence representing an amino acid position of the protein sequence and having an amino acid value chosen from one of a predetermined amino acid value and a missing value;

receiving an edge index of edge elements, each edge element of the edge index being associated to a respective pair of the node elements and having at least a presence value, a positive presence value indicating the presence of a physical interaction between the amino acid positions corresponding to the pair of node elements, the edge index thereby defining a desired fold structure of the protein sequence;

processing, by a computer-implemented neural network, a working copy of the partially filled sequence and the edge index to:

determine, for each given edge element of the edge index having a positive presence value, an enhanced edge attribute value set based on the amino acid values of the pair of node elements of the working copy sequence associated to the given edge element;

determine, for each given node element of the working copy sequence, an enhanced amino acid value based on the enhanced edge attribute value sets for every edge element having a positive presence value associated to the given node element; and for each given node element of the partially filled sequence having the missing value, determining a generated amino acid value based on the enhanced amino acid value corresponding to the given node element.

2. The method of claim 1, further comprising:

receiving an edge attribute dataset defining, for each edge element having a positive presence value, an edge attribute value set representing at least one characteristic of the physical interaction between the amino acid positions corresponding to the pair of node elements associated to the given edge element; and wherein the enhanced edge attribute value set for each given edge element of the edge index is initially determined based on the edge attribute value set for the given edge element in combination with the amino acid values of the pair of node elements of the working copy sequence associated to the given edge element.

3. The method of claim 2, wherein:

the edge attribute value set for each given edge element defines a Euclidian distance between the amino acid positions corresponding to the pair of node elements associated to the given edge element.

4. The method of claim 1, wherein:

the enhanced edge attribute value set for each given edge element is determined using one or more trained multi-layer perceptrons.

5. The method of claim 4, wherein:

the enhanced amino acid value for each given node element of the working copy sequence is determined in a pooling module from summing the enhanced edge attribute value sets for the edge elements having the positive presence value associated to the given node element.

6. The method of claim 5, wherein:

the neural network comprises a plurality of repeated residual blocks each encompassing a respective one of the one or more trained multi-layer perceptrons and a respective summing block; and wherein the enhanced edge attribute value sets and the enhanced amino acid values determined in a preceding one of the residual blocks are provided as inputs to a subsequent one of the residual blocks.

7. The method of claim 6, wherein:

in the subsequent one of the residual blocks, the enhanced edge attribute value set for each given edge element of the edge index is determined based on the enhanced edge attribute value set for the given edge element determined in the preceding one of the residual blocks in combination with the enhanced amino acid values of the pair of node elements associated to the given edge element determined in the preceding one of the residual blocks.

8. The method of claim 4, wherein:

the enhanced amino acid value for each given node element of the working copy sequence is determined in a pooling module from applying a weighted sum of the enhanced edge attribute value sets for the edge elements having the positive presence value associated to the given node element.

9. The method of claim 1, wherein:

the working copy sequence is mapped into an embedding space; and the processing by the neural network is carried out on the working copy sequence as mapped into the embedding space.

10. The method of claim 1, wherein:

the enhanced edge attribute value sets for the edge elements of the edge index are mapped into an embedding space; and wherein the processing by the neural network is carried out on the edge attribute value sets as mapped into the embedding space.

11. The method of claim 1, further comprising:

for each given node element of the partially filled sequence having the missing value, replacing the missing value by the generated amino acid value corresponding to the given node element; and whereby the partially filled sequence formed of the node elements having predetermined amino acid values and node elements having missing values replaced by the generated amino acid values represents a completed protein sequence.

12. The method of claim 1, wherein:

determining the generated amino acid value for each given node element of the partially filled sequence having the missing value comprises:

determining, for each of a plurality of possible amino acid values, a probability metric based on the enhanced amino acid value of the corresponding node element; and selecting the possible amino acid value having the highest probability metric as the generated amino acid value for the given node element of the partially filed sequence.

13. The method of claim 1, wherein:

an annotated training dataset for training the neural network comprises a plurality of protein sequence entries, each entry comprising:

an amino acid sequence of position elements each having a respective amino acid value;

an edge index indicating pairs of position elements of the amino acid sequence having a physical interaction; and the annotated training dataset further comprises an input subset and a target subset, wherein:

in the input subset, the amino acid values of a portion of the position elements of the amino acid sequences are masked; and in the target subset, the amino acid values of the position elements of amino acid sequences corresponding to the sequences of the input subset are non-masked.

14. The method of claim 13, wherein:

each entry of the annotated training dataset further comprises an edge attribute dataset defining, for each element of the edge index indicating the physical interaction, at least one characteristic of the physical interaction between the pair of position elements.

15. The method of claim 13, wherein:

the training of the neural network comprises adjusting parameters of the neural network to decrease, or minimize, the cross entropy loss between:

(i) amino acid values of outputted amino acid sequences as determined by the neural network applied to the input subset and (ii) the amino acid values of corresponding amino acid sequences of the target subset.

16. The method of claim 1, wherein the method scores mutations of specific residues, said mutations comprising substitutions, additions, and/or deletions of residues.

17. The method of claim 1, wherein the method generates a protein sequence based on one or more given protein folds.

18. A computer program product comprising a non-transitory storage medium having stored thereon computer-readable instructions, wherein the instructions when executed on a processor causes the processor to carry out the method according to claim 1.

19. A protein sequence generated by the method of claim 1.

20. A system comprising:

at least one memory; and at least one processor coupled to the memory, and being configured for performing:

receiving an empty or partially filled sequence of node elements, each node element of the sequence representing an amino acid position of the protein sequence and having an amino acid value chosen from one of a predetermined amino acid value and a missing value;

receiving an edge index of edge elements, each edge element of the edge index being associated to a respective pair of the node elements and having at least a presence value, a positive presence value indicating the presence of a physical interaction between the amino acid positions corresponding to the pair of node elements, the edge index thereby defining a desired fold structure of the protein sequence;

processing, by a computer-implemented neural network, a working copy of the partially filled sequence and the edge index to:

determine, for each given edge element of the edge index having a positive presence value, an enhanced edge attribute value set based on the amino acid values of the pair of node elements of the working copy sequence associated to the given edge element;

determine, for each given node element of the working copy sequence, an enhanced amino acid value based on the enhanced edge attribute value sets for every edge element having a positive presence value associated to the given node element; and for each given node element of the partially filled sequence having the missing value, determining a generated amino acid value based on the enhanced amino acid value corresponding to the given node element.

* * * * *